(12) United States Patent
Lee et al.

(10) Patent No.: US 11,002,990 B2
(45) Date of Patent: May 11, 2021

(54) EFFICIENT GESTURE-BASED CONTACT LENS ALGORITHMS FOR HUMAN TO CONTACT LENS COMMUNICATION

(71) Applicant: Verily Life Sciences LLC, Mountain View, CA (US)

(72) Inventors: Shungneng Lee, Sunnyvale, CA (US); Christian Gutierrez, San Francisco, CA (US); Tim English, Mountain View, CA (US); Brian Kim, West Hills, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 234 days.

(21) Appl. No.: 16/150,320

(22) Filed: Oct. 3, 2018

(65) Prior Publication Data

US 2019/0107734 A1 Apr. 11, 2019

Related U.S. Application Data

(60) Provisional application No. 62/570,282, filed on Oct. 10, 2017.

(51) Int. Cl.
*G02C 7/00* (2006.01)
*G02C 7/02* (2006.01)
(Continued)

(52) U.S. Cl.
CPC .............. *G02C 7/04* (2013.01); *A61B 5/053* (2013.01); *A61B 5/6821* (2013.01);
(Continued)

(58) Field of Classification Search
CPC .......... G02C 7/04; G02C 7/047; G02C 7/048; G02C 7/044; G02C 7/049; G02C 7/041;
(Continued)

(56) References Cited

U.S. PATENT DOCUMENTS 5,682,210 A 10/1997 Weirich
8,280,484 B2 * 10/2012 Boyden ............. A61M 5/14276
600/407
(Continued)

FOREIGN PATENT DOCUMENTS

WO 2013059656 A2 4/2013

OTHER PUBLICATIONS

International Search Report of International Application No. PCT/US2018/053907, dated Nov. 15, 2018.

*Primary Examiner* — William R Alexander
*Assistant Examiner* — Tamara Y. Washington
(74) *Attorney, Agent, or Firm* — McDonnell Boehnen Hulbert & Berghoff

(57) ABSTRACT

An eye-mountable device is provided that includes an eyelid occlusion sensor. The eyelid occlusion sensor is used to detect winks, squints, downwards glances or looks, blinks, or other eye-based gestures generated by the user. Based on the detected gestures, an optical power of an adjustable lens of the device may be changed or some other operations could be performed by the eye-mountable device. Such operations could include toggling the optical power of the lens between first and second power levels due to the user squinting, looking downward, or performing some other gesture. Additionally or alternatively, such operations could include setting the optical power of the lens to a first optical power unless the user is looking downward, in which case the optical power of the lens could be set to a second optical power.

15 Claims, 9 Drawing Sheets

(51) Int. Cl.
*G02C 7/04* (2006.01)
*A61F 2/16* (2006.01)
*A61B 5/00* (2006.01)
*G02C 7/08* (2006.01)
*A61B 5/053* (2021.01)
*G02C 11/00* (2006.01)
*A61B 3/113* (2006.01)
*A61B 5/145* (2006.01)
*A61F 2/48* (2006.01)

(52) U.S. Cl.
CPC .......... *A61F 2/1624* (2013.01); *G02C 7/083* (2013.01); *A61B 3/113* (2013.01); *A61B 5/14542* (2013.01); *A61F 2002/482* (2013.01); *A61F 2250/0002* (2013.01); *G02C 7/081* (2013.01); *G02C 11/10* (2013.01)

(58) Field of Classification Search
CPC ...... G03B 17/565; G03H 1/00; G03H 1/2294; G03H 2001/085; G06K 9/00275; G02B 1/043; G02B 1/041; G02B 2027/0174; G02B 13/0025; A61F 2/1618; A61F 2/1613; A61F 2/1637; A61F 2/1654; C08L 83/04; C08L 101/14; C08L 33/08; C08L 33/10; B29D 11/00028; B29D 11/00038; B29D 11/00807; A61B 34/10; A61B 3/0025; A61B 3/0033; A61B 3/0041; A61B 3/02; A61B 3/112
USPC ................. 359/159.14; 351/159.14
See application file for complete search history.

(56) References Cited

U.S. PATENT DOCUMENTS

| | | | |
|---|---|---|---|
| 8,820,934 | B1 | 9/2014 | Ho et al. |
| 9,072,465 | B2 | 7/2015 | Pugh et al. |
| 9,241,669 | B2 | 1/2016 | Pugh et al. |
| 9,468,372 | B2 | 10/2016 | Pugh et al. |
| 10,165,941 | B2 * | 1/2019 | Walsh .......... A61B 3/102 |
| 2006/0025897 | A1 | 2/2006 | Shostak et al. |
| 2010/0016704 | A1 | 1/2010 | Naber et al. |
| 2012/0019662 | A1 | 1/2012 | Maltz |
| 2013/0258287 | A1 | 10/2013 | Pugh et al. |
| 2014/0081178 | A1 | 3/2014 | Pletcher et al. |
| 2014/0156000 | A1 | 6/2014 | Campin et al. |
| 2014/0240655 | A1 | 8/2014 | Pugh et al. |
| 2016/0097940 | A1 | 4/2016 | Sako et al. |
| 2017/0097519 | A1 | 4/2017 | Lee |
| 2017/0190127 | A1 | 7/2017 | Kinser et al. |

* cited by examiner

EFFICIENT GESTURE-BASED CONTACT LENS ALGORITHMS FOR HUMAN TO CONTACT LENS COMMUNICATION

CROSS-REFERENCE TO RELATED APPLICATION

This application claims priority to U.S. Provisional Patent Application No. 62/570,282, filed Oct. 10, 2017, which is incorporated herein by reference.

BACKGROUND

Unless otherwise indicated herein, the materials described in this section are not prior art to the claims in this application and are not admitted to be prior art by inclusion in this section.

An eye-mountable device may include sensors, adjustable lenses, electronics, or other components configured to provide a controllable optical power, to obtain health-related information (e.g., based on a flow rate or level of oxygenation of blood in vasculature of an eye), or to provide some other functionality to a user wearing the eye-mountable device. Such an eye-mountable device may include a sensor apparatus configured to detect physiological properties of a wearer and/or properties of the environment of a wearer. Additionally or alternatively, such an eye-mountable device may include a liquid crystal lens, electrowetting lens, or some other type of adjustable lens to provide a controllable optical power to an eye. In some examples, the eye-mountable device may be in the form of a contact lens that includes a sensor apparatus configured to detect a property of interest.

SUMMARY

Some embodiments of the present disclosure provide an ophthalmic device that includes: (i) an eyelid occlusion sensor; (ii) an adjustable lens; and (iii) a controller. The controller includes electronics that perform operations including: (a) detecting, at a plurality of points in time, an output of the eyelid occlusion sensor; (b) determining, based on the detected output of the eyelid occlusion sensor, that a degree of occlusion of an eye increases during a first period of time; (c) determining that a detected output of the eyelid occlusion sensor at a first point in time differs from a detected output of the eyelid occlusion sensor at a second point in time by less than a specified amount, wherein the second point in time is after the first period of time; and (d) responsive to determining that the detected output of the eyelid occlusion sensor at the first point in time differs from the detected output of the eyelid occlusion sensor at the second point in time by less than the specified amount, adjusting an optical power of the adjustable lens.

Some embodiments of the present disclosure provide an ophthalmic device that includes: (i) an eyelid occlusion sensor; (ii) an adjustable lens; and (iii) a controller. The controller includes electronics that perform operations including: (a) detecting, at a plurality of points in time, an output of the eyelid occlusion sensor; (b) determining, at a first point in time based on the detected output of the eyelid occlusion sensor, that a level of noise in the output of the eyelid occlusion sensor during a specified period of time prior to the first point in time is below a specified level; (c) determining that a detected output of the eyelid occlusion sensor at the first point in time exceeds a first threshold; and (d) adjusting an optical power of the adjustable lens responsive to determining that the detected output of the eyelid occlusion sensor at the first point in time exceeds the first threshold and that the level of noise in the output of the eyelid occlusion sensor during the specified period of time prior to the first point in time is below the specified level.

Some embodiments of the present disclosure provide an ophthalmic device that includes: (i) an eyelid occlusion sensor; (ii) an adjustable lens; and (iii) a controller. The controller includes electronics that perform operations including: (a) detecting, at a plurality of points in time, an output of the eyelid occlusion sensor; (b) determining, based on the detected output of the eyelid occlusion sensor, that a first gesture has occurred; (c) responsive to determining that the first gesture has occurred, switching the optical power of the adjustable lens between a first optical power and a second optical power, wherein the first optical power is different than the second optical power; (d) determining, based on the detected output of the eyelid occlusion sensor, that a second gesture has occurred; and (e) responsive to determining that the second gesture has occurred, setting the optical power of the adjustable lens to the first optical power.

Some embodiments of the present disclosure provide a method including: (i) detecting, at a plurality of points in time, an output of an eyelid occlusion sensor; (ii) determining, based on the detected output of the eyelid occlusion sensor, that a first gesture has occurred; (iii) responsive to determining that the first gesture has occurred, switching the optical power of an adjustable lens between a first optical power and a second optical power, wherein the first optical power is different than the second optical power; (iv) determining, based on the detected output of the eyelid occlusion sensor, that a second gesture has occurred; and (v) responsive to determining that the second gesture has occurred, setting the optical power of the adjustable lens to the first optical power.

These as well as other aspects, advantages, and alternatives, will become apparent to those of ordinary skill in the art by reading the following detailed description, with reference where appropriate to the accompanying drawings.

DETAILED DESCRIPTION

Figure 1A:
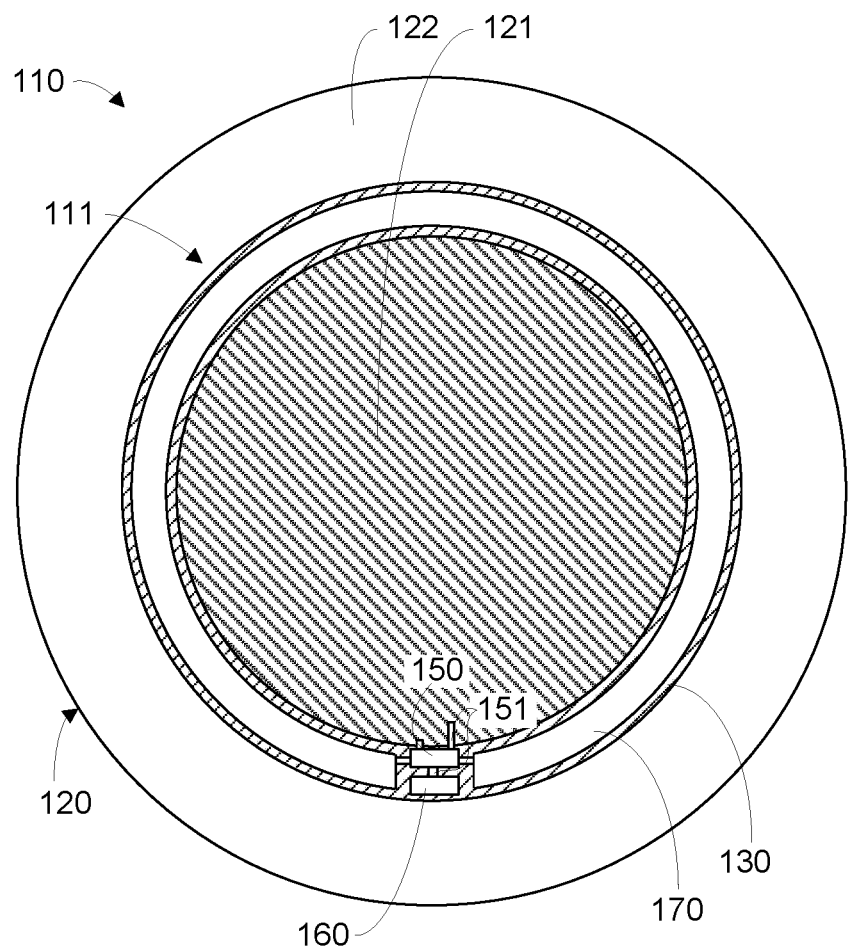
FIG. 1A is a top view of an example eye-mountable ophthalmic device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

It can be beneficial in a variety of applications to be able to control the optical power (e.g., diopter, focal length) of a lens. For example, the ability to control the optical power of a contact lens or eyeglasses could allow such devices to compensate for a diminished or lost ability of a person's eye to naturally accommodate. Accommodation is a process by which the optical properties of a person's eye (e.g., the focal length of the crystalline lens of the eye) are controlled to allow the eye to focus on objects at different distances from the eye at different points in time. The ability of a person's eye to accommodate may be diminished by age, lost completely due to removal or the crystalline lens (e.g., as a result of cataract surgery), or diminished or lost for some other reason.

An adjustable lens could have an optical power (e.g., a diopter, a focal length) that is controllable. The optical power of such an adjustable lens could be mechanically controllable, e.g., by the application of a mechanical force or pressure to deform one or more refractive, reflective, or diffractive elements of the lens, by the application of a hydraulic or pneumatic pressure to change a volume or geometry of an element by adding or subtracting fluid from the volume or controlling a pressure of a fluid within the volume, or by exerting some other mechanical force(s) to control or change the optical power of the adjustable lens. Additionally or alternatively, an adjustable lens could be electronically controllable, e.g., by the application of an electrical or magnetic field to change an optical property of a material of the lens, by applying an electrical field or current to control the geometry of a volume of fluid within the lens, by applying an electrical field to control the refractive index of one or more elements of the lens, or by exerting some other electrical field(s) or force(s) to control or change the optical power of the adjustable lens.

Such an adjustable lens could be incorporated into an ophthalmic device designed to be disposed on or within an eye and to provide a controllable optical power to the eye. Such an ophthalmic device could be an eye-mountable device, such as a contact lens. Alternatively, such an ophthalmic device could be an implantable device, e.g., a device configured to be implanted within a lens capsule of an eye. Such an ophthalmic device could include one or more controllers, sensors, or other electronic components to facilitate operation of the adjustable lens to provide a controllable optical power to an eye to which the device is mounted and/or in which the device is implanted. The provided optical power could be controlled to compensate for a reduced ability of the eye to accommodate. For example, the provided optical power could be controlled to facilitate viewing of near objects when the eye is looking at an object near the eye, and to facilitate viewing of far objects when the eye is looking at an object far from the eye. The ophthalmic device could include sensors to detect a distance of objects from the device, a vergence of the eye relative to another eye, a pupillary diameter, or some other physical variable that may be related to an optical power that it could be beneficial for the ophthalmic device to provide.

In some examples, the ophthalmic device could include one or more sensors configured to detect a degree of occlusion of the sensor(s) and/or of the ophthalmic device by one or both of a wearer's eyelids or to detect some other process related to gestures that a user may produce using their eye(s). Such occlusion could include occlusion of the sensor(s) due to the wearer squinting or blinking. Additionally or alternatively, such occlusion could include occlusion of the sensor(s) due to the wearer looking upward, downward, or in some other direction such that the sensor is located beneath an eyelid or other accessory tissue of an eye. The degree of occlusion could be sensed by an eyelid occlusion sensor and used to operate the adjustable lens. For example, the degree of occlusion could be sensed and used to determine that a user has blinked, squinted, looked downward, changed a direction of gaze, or engaged in some other volitional, reflex, or other movement of their eye and/or eyelids. Such movements could form elements of one or more eye-based gestures that could be detected based on outputs of the sensor. Based on such detected movements, the optical power of the adjustable lens could be controlled.

In some examples, the ophthalmic device could detect, using an eyelid occlusion sensor, that a wearer is looking downward and responsively set the optical power of the adjustable lens to facilitate viewing of near objects (e.g., to facilitate reading). In response to detecting that the wearer is no longer looking downward, the optical power of the adjustable lens could be set to facilitate viewing of far objects. Alternatively, the optical power of the adjustable lens could remain set to facilitate viewing of near objects until another condition is detected (e.g., the wearer squinting for a specified period of time, looking downward, blinking, or performing some other movement). Additionally or alternatively, the degree of occlusion of a sensor could be detected and used to detect that a wearer is squinting. The optical power of the adjustable lens could be set, responsive to detecting that the wearer has been squinting for a specified period of time, to facilitate viewing of near objects (e.g., to facilitate reading). In response to detecting that the wearer is squinting again, looking downward, blinking, or performing some other movement, the optical power of the adjustable lens could be set to facilitate viewing of far objects. Additional or alternative movements and/or eye-based gestures could be detected using such a sensor and could be used, via a variety of different user interface schemes, to operate an adjustable lens.

II. Example Eye-Mountable Ophthalmic Device

An adjustable lens and eyelid occlusion sensor as described herein could be incorporated into an eye-mountable device or into some other ophthalmic device. Such an ophthalmic device could additionally include an electronic apparatus (e.g., one or more sensors, controllers, batteries, antennas, or other elements) that, along with the adjustable lens, is encapsulated within a rigid, gas permeable polymer layer, a soft polymer layer, or within some other encapsulating material. Such encapsulation could provide protection and/or structure to the lens and electronic apparatus, an overall shape or external mounting surface of the eye-mountable and/or implantable device, and/or some other benefit. An ophthalmic device including an adjustable lens can be configured or operated to provide a controllable optical power to an eye and/or some other applications (e.g., sensing a level of blood oxygenation or other physiological parameters of a wearer, detecting blinks or other user inputs or actions, providing power to a device implanted within an eye).

Note that aspects of the example ophthalimic devices described herein (e.g., eyelid occlusion sensors, controllers, power sources, adjustable lenses, methods of operation) could be applied without limitation to eye-mountable devices, implantable devices, or otherwise configured ophthalmic devices configured to provide a controllable optical power, or some other benefit, to an eye.

A polymer layer (or other material) within which elements of an adjustable lens (one or more lenses, lens chambers, electrodes, volumes of immiscible fluids, and/or volumes of liquid crystal), electronics, sensors, interconnects, and/or other components are encapsulated could be formed to be removably mounted directly to an eye in a manner that is compatible with eyelid motion (e.g., the polymer layer could be formed as a soft or rigid contact lens). Alternatively, such a polymer layer (e.g., a rigid, gas-permeable polymer layer) could be embedded within some further encapsulating material (e.g., within a hydrogel or other soft or rigid polymer layer formed to mount to an eye) and/or could be formed to mount to or within a soft polymer layer that is configured to mount to an eye in combination with the polymer layer containing the electroactive lens.

Figure 1B:
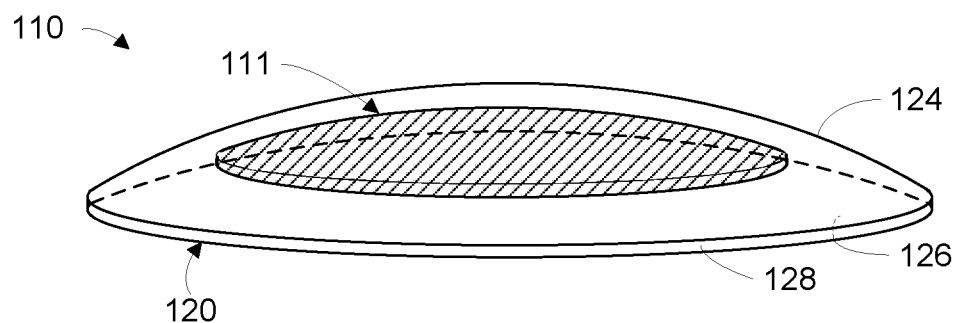
FIG. 1B is an aspect view of the example eye-mountable ophthalmic device shown in FIG. 1A.

FIG. 1A is a top view of an example eye-mountable ophthalmic device 110. FIG. 1B is an aspect view of the example eye-mountable ophthalmic device shown in FIG. 1A. It is noted that relative dimensions in FIGS. 1A and 1B are not necessarily to scale, but have been rendered for purposes of explanation only in describing the arrangement of the example eye-mountable ophthalmic device 110. The eye-mountable ophthalmic device 110 includes an electronic apparatus 111 embedded within a polymer layer 120. The electronic apparatus 111 includes an adjustable lens 121. Components of the electronic apparatus 111 may be embedded (e.g., fully encapsulated within a rigid, gas-permeable polymer layer or other material to provide mechanical stability to the electronic apparatus 111, to prevent exposure of components of the electronic apparatus 111 to water or other substances in an environment of the eye-mountable ophthalmic device 110, or to provide some other benefit. The polymer layer 120 could comprise such a rigid, gas-permeable polymer layer; alternatively, the rigid, gas-permeable polymer layer could be embedded within the polymer layer 120 (e.g., within a soft hydrogel of the polymer layer 120).

The polymer layer 120 can be shaped as a curved disk. The polymer layer 120, elements of the electronic apparatus 111 (e.g., lenses, lens chambers, electrodes, liquid crystals, immiscible fluids), or other components of the eye-mountable ophthalmic device 110 can be composed of substantially transparent material(s) to allow incident light to be transmitted to the eye while the eye-mountable ophthalmic device 110 is mounted to the eye. The polymer layer 120 can be a biocompatible, oxygen-permeable material similar to those employed to form soft vision correction and/or cosmetic contact lenses in optometry, such as a silicone hydrogel. Additionally or alternatively, a rigid, gas-permeable polymer layer encapsulating the electronic apparatus 111 and/or one or more lenses or other elements of the adjustable lens 121 could be composed of a biocompatible, oxygen-permeable material like silicone acrylate, fluoro-silicone acrylate, or some other rigid, gas-permeable polymers. The polymer layer 120 and/or one or more lenses or other elements of the adjustable lens 121 could include further compounds or materials to provide some functionality, e.g., to block ultraviolet light from being transmitted, through the eye-mountable ophthalmic device 110, to an eye. Further, the polymer layer 120 could include a surface coating configured to provide some functionality, e.g., a hydrophilic coating or some other coating to increase wetting and/or comfort.

The polymer layer 120 can be formed with one side having a concave surface 126 suitable to fit over a corneal surface of an eye. The opposing side of the disk can have a convex surface 124 that does not interfere with eyelid motion when the eye-mountable ophthalmic device 110 is mounted to the eye. A circular outer side edge 128 connects the concave surface 124 and convex surface 126. The eye-mountable ophthalmic device 110 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable ophthalmic device 110 can be selected according to the size and/or shape of the corneal surface of the wearer's eye. The shape of the eye-mountable ophthalmic device 110 can be specified with a curvature, astigmatism, or other properties to provide a specified optical power to an eye. Additionally or alternatively, the shape of the eye-mountable ophthalmic device 110 could be specified to apply a force to a cornea of an eye to which the eye-mountable ophthalmic device 110 is mounted, e.g., to correct keratoconus or according to some other application.

The polymer layer 120 can be formed with a curved shape in a variety of ways. For example, techniques similar to those employed to form vision-correction contact lenses can be employed to form the soft polymer layer 120. These methods can include molding, machining, lathing, polishing, or other processes. While the eye-mountable ophthalmic device 110 is mounted on an eye, the convex surface 124 faces outward to the ambient environment while the concave surface 126 faces inward, toward the corneal surface. The convex surface 124 can therefore be considered an outer, top surface of the eye-mountable ophthalmic device 110 whereas the concave surface 126 can be considered an inner, bottom surface. The "top" view shown in FIG. 1A is facing the convex surface 124. From the top view shown in FIG. 1A, the outer periphery 122, near the outer circumference of the curved disk is curved into the page, whereas the center region, corresponding to the location of the electroactive lens 121, near the center of the disk is curved out of the page.

An electronic apparatus 111 is embedded within the polymer layer 120. The electronic apparatus 111 includes the central adjustable lens 121 surrounded by a substrate 130. The adjustable lens 121 and substrate 130 can be embedded such that the substrate 130 is situated along the outer periphery of the polymer layer 120, away from the center region of the eye-mountable ophthalmic device 110. The substrate 130 does not interfere with vision because it is too close to the eye to be in focus and is positioned away from the center region of the adjustable lens 121 where incident light is transmitted, through the adjustable lens 121, to the light-sensing portions of the eye. Moreover, the substrate 130 can be formed of a transparent material to further mitigate any effects on visual perception. In some examples, the substrate 130 could be formed from and/or disposed on an element of the adjustable lens 121. For example, a particular lens or other element of the adjustable lens 121 could include a peripheral region on which electronics can be disposed and/or on which metallic traces, electrodes, antennas, interconnects, or other conductive elements (e.g., conductive elements for electrically coupling electronics to electrodes or other elements of the adjustable lens 121) can be formed.

The substrate 130 can be shaped as a flat, circular ring (e.g., a disk with a central hole). The flat surface of the substrate 130 (e.g., along the radial width) is a platform for mounting electronics such as chips (e.g., via flip-chip mounting) and for patterning conductive materials (e.g., via deposition techniques) to form electrodes (e.g., an anode and/or cathode of an electrochemical battery, electrodes for detecting an impedance of a tear film or other tissues, electrodes of an electrochemical sensor, contact electrodes for electrically contacting with leads of the adjustable lens 121), conductive loops (e.g., a conductive loop of an eyelid occlusion sensor), antenna(e), and/or connections. The substrate 130, adjustable lens 121, and/or the polymer layer 120 can be approximately cylindrically symmetric about a common central axis. The substrate 130 can be implemented in a variety of different form factors.

A conductive loop 170, controller 150, and sensor 160 are disposed on the embedded substrate 130. The controller 150 can be a chip including logic elements configured to detect an occlusion of the eye-mountable ophthalmic device using the conductive loop 170 and/or sensor 160, to receive wireless power using the conductive loop 170, to send and/or receive wireless communications using the conductive loop 170, to operate the sensor 160, and to provide a controllable optical power using the adjustable lens 121. The controller 150 is electrically connected to the conductive loop 170, sensor 160, and adjustable lens 121 (e.g., to conductive leads or electrodes of the adjustable lens 121) by interconnects 151 that may be wholly or partially situated on the substrate 130. Additional or alternative components could be disposed on the substrate 130, e.g., an electrochemical battery could be provided on the substrate 130 to power the eye-mountable ophthalmic device 110.

The interconnects 151, the conductive loop 170, and any conductive electrodes (e.g., an anode and cathode of an electrochemical battery, electrodes of an impedance sensor configured to detect an impedance through a tear film or other tissues, for an electrochemical ion sensor, etc.) can be formed from conductive materials patterned on the substrate 130 by a process for precisely patterning such materials, such as deposition, lithography, etc. In embodiments wherein the substrate 130 is part of a lens or other element(s) of the adjustable lens 121, electrode(s) of the adjustable lens 121 could be formed on the lens or other element(s) of the adjustable lens 121 via such processes.

The conductive materials patterned on the substrate 130 can be, for example, gold, platinum, palladium, titanium, carbon, aluminum, copper, silver, silver-chloride, conductors formed from noble materials, metals, combinations of these, etc. Electrode(s) of the adjustable lens 121 could be electrically coupled to the controller 150 or other electronic components of the eye-mountable ophthalmic device 110 via such interconnects 151 and/or via wires, conductive adhesives, liquid crystal, or some other interconnecting means.

The sensor 160 could include a variety of components configured to detect one or more physical variables of interest, e.g., a light level, a bioelectric field, a spectrum of light received from vasculature of an eye. In some examples, the sensed variable could be related to one or more parameters of a body (e.g., an amount of blood in a portion of subsurface vasculature, an oxygenation state of blood, to what degree an eyelid is occluding the sensor 160), properties of the environment of the device (e.g., an ambient illumination, a barometric pressure, a temperature), properties of the device (e.g., an acceleration, an orientation), or to detect some other information. Such sensors could include accelerometers, electrodes (e.g., electrodes of an electrophysiological sensor configured to detect an electrooculogram, an electromyogram, or some other bioelectrical signal), light detectors, thermometers, gyroscopes, capacitance sensors, pressure sensors, strain gauges, light emitters, microphones, or other elements configured to detect one or more physical variables related to a property of interest. Variables detected using the sensor 160 could be used to control an optical power of the adjustable lens 121. For example, the detected variables could be related to a vergence of an eye (e.g., relative to another eye), a distance between the eye-mountable ophthalmic device 110 and an object in an environment of a wearer, an electrical activity of the ciliary muscles or other muscles of an eye, a pupillary diameter, a degree of occlusion of the eye-mountable ophthalmic device 110, or some other variable(s) that could be used to determine, e.g., a desired optical power to provide to an eye of a wearer.

The eye-mountable ophthalmic device 110 includes an eyelid occlusion sensor. The eyelid occlusion sensor includes one or more sensors that generate an output (e.g., a voltage, a current, a binary digital value) related to a degree of occlusion of the one or more sensors and/or of the eye-mountable ophthalmic device 110 by one or more eyelids or other tissues of or proximate to an eye. Such an eyelid occlusion sensor could include one or both of the sensor 160 or conductive loop 170 or could include additional or alternative elements. For example, the eyelid occlusion sensor could include a light-sensitive element (e.g., a photodiode, a photoresistor) of the sensor 160 and could operate to generate an output related to a degree of occlusion of the sensor 160 by using the light-sensitive element to detect an intensity or other property of light received by the light sensitive element. In some examples, the eye-mountable ophthalmic device 110 could include additional light-sensitive elements (e.g., disposed at respective locations around the substrate 130) and the eyelid occlusion sensor could use the additional light-sensitive elements to detect a degree of occlusion of the eye-mountable ophthalmic device 110, e.g., by detecting a sum or other property of the light detected by the additional light-sensitive elements, by determining how many of the additional light-sensitive elements are receiving more than a threshold amount of light, or by some other method.

In another example, the eyelid occlusion sensor could include the conductive loop 170 and could use the conductive loop to generate an output related to a degree of occlusion of the eye-mountable ophthalmic device 110. An impedance magnitude, real impedance, imaginary impedance, inductance, capacitance, resistance, quality-factor, resonance frequency, or some other property of the conductive loop 170 could be related to the degree of occlusion of the eye-mountable ophthalmic device 110 and the eyelid sensor could operate to detect such a property of the conductive loop 170. This could include applying a specified voltage and/or current waveform to the conductive loop 170 and detecting a property (e.g., a current, a voltage) of the response of the conductive loop 170 to the applied current and/or voltage.

In the example shown in FIGS. 1A-B, the adjustable lens 121 and other elements of the electronic apparatus are fully encapsulated within the polymer layer 120; that is, the polymer layer 120 completely surrounds the electronic apparatus 111 such that no aspect or element of the electronic apparatus 111 is exposed to an environment of the eye-mountable ophthalmic device 110 (e.g., to a tear fluid of an eye to which the eye-mountable ophthalmic device 110 is mounted). However, this is intended as a non-limiting example embodiment. In other embodiments, one or more volumes of liquid crystal, one or more fluids disposed in an electrowetting lens, or other elements of the adjustable lens 121, the controller 150, the conductive loop 130, the sensor 160, the interconnects 151, the substrate 130, an adhesive applied to the adjustable lens 121 or to some other component(s), or some other elements of the eye-mountable ophthalmic device could be fully encapsulated within a combination of the polymer layer 120 and some other component(s) of the eye-mountable ophthalmic device 110 (e.g., within a rigid, gas-permeable polymer layer that is, itself, embedded within a soft polymeric material of the polymer layer 120) such that the fully encapsulated components are protected from ingress of moisture or other substances or are provided with some other benefit related to being fully encapsulated.

For example, the polymer layer 120 could be formed by placing the adjustable lens 121, substrate 130, and components disposed on the substrate 130 in a mold, filling the mold with a precursor material (e.g., a solution of monomer units), and curing the precursor solution. The mold could include a number of support features that are in contact with a particular lens or other element of the adjustable lens 121, e.g., to provide support to the adjustable lens 121 while casting a rigid, gas-permeable polymeric material or other material or elements of the polymer layer 120, to control a location of the adjustable lens 121 within the formed polymer layer 120, or to provide some other benefit. In such an example, one or more locations of the particular lens, corresponding to the locations at which the particular lens was contacted by the support features of the mold, may be exposed following formation of the polymer layer 120. Thus, the particular lens of the adjustable lens 121 is not fully encapsulated within the formed polymer layer 120. However, other elements of the eye-mountable ophthalmic device, including the controller 150, the interconnects 151, one or more volumes of liquid crystal, immiscible fluids, and/or further lenses or other elements of the adjustable lens 121, the sensor 160, or the conductive loop 170 are fully encapsulated within the combination of the polymer layer 120 and the particular lens of the adjustable lens 121.

As shown in FIG. 1A, the controller 150 and sensor 160 are mounted to a side of the substrate 130 facing the convex surface 124. However, the electronics, sensor, interconnects, etc. situated on the substrate 130 can be mounted to either the "inward" facing side (e.g., situated closest to the concave surface 126) or the "outward" facing side (e.g., situated closest to the convex surface 124). Moreover, in some embodiments, some electronic components can be mounted on one side of the substrate 130, while other electronic components are mounted to the opposing side, and connections between the two can be made via conductive materials passing through the substrate 130.

The conductive loop 170 can be a layer of conductive material patterned along the flat surface of the substrate to form a flat conductive ring. In some instances, the conductive loop 170 can be formed without making a complete loop. For instance, the conductive loop 170 can have a cutout to allow room for the controller 150 and sensor 160, as illustrated in FIG. 1A. However, the conductive loop 170 can also be arranged as a continuous strip of conductive material that wraps entirely around the flat surface of the substrate 130 one or more times. For example, a strip of conductive material with multiple windings can be patterned on the side of the substrate 130 opposite the controller 150 and sensor 160. Interconnects between the ends of such a wound conductive loop can be passed through the substrate 130 to the controller 150.

Note that the eye-mountable ophthalmic device 110 illustrated in FIGS. 1A-B is intended as a non-limiting example embodiment. An eye-mountable or otherwise configured ophthalmic device that includes an electronic apparatus at least partially embedded within a polymer layer could include additional or alternative elements to those shown in FIGS. 1A-B, or could lack some of the elements shown in FIGS. 1A-B. For example, such an eye-mountable ophthalmic device could include only one of a conductive loop or a further discrete sensor to facilitate detection of a degree of occlusion of the device and/or portions thereof by an eyelid or other tissues accessory to an eye. Further, while elements of the eye-mountable ophthalmic device 110 shown in FIGS. 1A-B are fully encapsulated within the polymer layer 120, an eye-mountable, an implantable, or an otherwise-configured ophthalmic device as described herein could include an electronic apparatus that is only partially embedded within a rigid and/or soft polymer layer. For example, one or more channels, windows, or other features could be formed in such polymer layer(s) to expose electrodes, sensors, or other elements of such a partially embedded electronic apparatus to an environment of such an ophthalmic device.

Still further, while the eye-mountable ophthalmic device 110 illustrated in FIGS. 1A-B includes an electronic apparatus 111 embedded within a polymer layer 120 that is formed to mount directly to an eye, an eye-mountable ophthalmic device could be configured differently and/or include additional or alternative elements configured to facilitate mounting of the eye-mountable ophthalmic device to an eye. For example, the polymer layer 120 could be one or the other of a soft polymer layer (e.g., a hydrogel) or a rigid, gas permeable polymer layer that is shaped to mount directly to an eye (e.g., could have a shape similar to the illustrated polymer layer 120). In some examples, a rigid, gas permeable polymer layer of the device 110 (e.g., that encapsulates the electronic apparatus 111) could be shaped such that the rigid, gas permeable polymer layer can be mounted on or within the a soft polymeric material of the polymer layer 120 such that the combination of the rigid, gas permeable polymer layer and the soft polymeric material can be removably mounted to an eye in a manner that is compatible with eyelid motion. The soft polymeric material and the rigid, gas permeable polymer layer could be configured in this way to permit reuse of the rigid, gas permeable polymer layer and electronic apparatus 111 encapsulated therein, to permit dry storage of the rigid, gas permeable polymer layer and electronic apparatus therein 111 (e.g., to reduce a rate of degradation of a chemical sensor of the electronic apparatus, to reduce a rate of degradation of a liquid crystal or other fluids of the adjustable lens 121), or to provide some other benefit.

Such a rigid, gas permeable polymer layer could be configured to be mounted on or within the polymer layer 120 in a variety of ways, e.g., via capillary forces, via an adhesive, via formed prongs, clips, ridges, or other formed elements in one or both of the polymer layer 120 and/or the rigid, gas-permeable polymer layer, or using some other means to mount the rigid, gas permeable polymer layer on or within the polymer layer 120. The rigid, gas permeable polymer layer and polymer layer 120 could be configured such that, when the rigid, gas permeable polymer layer is mounted to the polymer layer 120, the rigid, gas permeable polymer layer is fully encapsulated within the polymer layer 120 or such that the rigid, gas permeable polymer layer is only partially encapsulated within the polymer layer 120 (e.g., such that an outer surface of the rigid, gas permeable polymer layer is in contact with a corneal surface or an inner eyelid surface of an eye when the rigid, gas permeable polymer layer is mounted to the polymer layer 120 and the combination of the rigid polymer layer and the polymer layer 120 is mounted to the eye).

The electronically adjustable lens 121 is configured such that a voltage, current, or other property of an electrical signal applied to the adjustable lens 121 can be controlled to control the optical power of the electronically adjustable lens 121. In some examples, this could include applying a voltage across a layer of liquid crystal of the adjustable lens 121 to, e.g., control a refractive index of the liquid crystal. In other examples, the adjustable lens 121 could include an electrowetting lens, e.g., could include two or more immiscible fluids, which differ with respect to refractive index, disposed within a lens chamber. Controlling the optical power of such an adjustable lens 121 could include applying a voltage to one or more electrodes in contact with the immiscible fluids to control a geometry of an interface between the fluids. The adjustable lens 121 could include other components configured to provide a controllable optical power through some other method or process (e.g., by electronically controlling a flow of a fluid, by using magnetic fields to exert forces on magnetically active fluids, by using one or more piezo elements or other actuators to deform, translate, or rotate one or more lenses or other optical elements).

The adjustable lens 121 could include additional elements, e.g., electrodes to apply a voltage or current to a liquid crystal, to two or more immiscible fluids within a lens chamber of an electrowetting lens, and/or to some other element of the adjustable lens 121, one or more layers of material configured to contain and/or provide structure to other elements of the adjustable lens 121 (e.g., one or more rigid layers, formed as lenses, that contain a liquid crystal and that include a texture configure to align the liquid crystal relative to the rigid layers, a lens chamber containing two or more immiscible fluids), or other components. In some examples, the adjustable lens 121 could include one or more elements (e.g., one or more textured, rigid layers on which electrodes are disposed) composed of a rigid, gas permeable polymeric material, e.g., of the same material from which a rigid, gas permeable polymer layer encapsulating the electronic apparatus 111 is formed.

The adjustable lens 121 could include two or more lenses between which are disposed one or more volumes of liquid crystal. For example, the adjustable lens 121 could include stacked first, second, and third lenses, a first volume of liquid crystal disposed between the first and second lenses, and a second volume of liquid crystal disposed between the second and third lenses. Such an adjustable lens, including two separate volumes of liquid crystal, could be configured such that anisotropy in the optical effects of the liquid crystal is at least partially compensated for by providing the anisotropic optical effect in a first direction using the first volume of liquid crystal and also providing the anisotropic effect in a second, perpendicular direction using the second volume of liquid crystal. Two or more electrodes could also be provided (e.g., deposited or otherwise formed on one or more of the lenses) to apply an electrical field or other electrical force or energy to the volume(s) of liquid crystal of the adjustable lens 121 to control the optical power (e.g., the diopter, the focal length) of the adjustable lens 121.

Figure 2A:
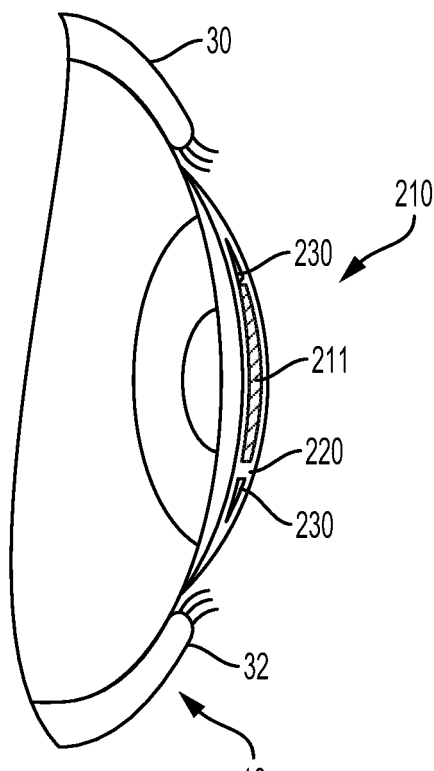
FIG. 2A is a side cross-section view of an example eye-mountable ophthalmic device while mounted to a corneal surface of an eye.

FIG. 2A is a side cross-section view of an example eye-mountable ophthalmic device 210 while mounted to a corneal surface of an eye 10. It is noted that relative dimensions in FIG. 2 are not necessarily to scale, but have been rendered for purposes of explanation only in describing the arrangement of the example eye-mountable ophthalmic device 210. Some aspects are exaggerated to allow for illustration and to facilitate explanation. The eye-mountable ophthalmic device 210 includes an adjustable lens 211. The eye-mountable ophthalmic device 210 also includes electronics 230 configured to operate the adjustable lens 211. The electronics 230 and the adjustable lens 211 are embedded in a polymer layer 220 (e.g., a layer comprising a rigid, gas-permeable polymeric material and/or a hydrogel or other soft polymeric material). The electronics 230 could be disposed around the adjustable lens 211 (e.g., on a ring-shaped substrate) and/or disposed on a lens or other element of the lens 211. The electronics include an eyelid occlusion sensor configured to detect a degree of occlusion of the eyelid occlusion sensor and/or of the eye-mountable ophthalmic device 210 by one or more eyelids or other tissues associated with the eye 10.

The eye 10 may be wholly or partially covered by an upper eyelid 30 and a lower eyelid 32. Incident light is received by the eye 10 through the adjustable lens 221, the polymer layer 220, and the cornea of the eye 20, where light is optically directed to light sensing elements of the eye 10 (e.g., rods and cones, etc.) to stimulate visual perception. The motion of the eyelids 30, 32 distributes a tear film across the exposed corneal surface of the eye 10. The tear film is an aqueous fluid secreted by the lacrimal gland to protect and lubricate the eye 10. The tear film layers are distributed across the corneal surface and/or external surfaces of the device 210 by motion of the eyelids 30, 32. For example, the eyelids 30, 32 raise and lower, respectively, to spread a small volume of tear film across the corneal surface and/or the external surfaces of the eye-mountable ophthalmic device 210. The tear film layer on the corneal surface also facilitates mounting the eye-mountable ophthalmic device 210 by capillary forces between a concave external surface the device 210 and the corneal surface. In some embodiments, the eye-mountable ophthalmic device 210 can also be held over the eye in part by vacuum forces against corneal surface due to the concave curvature of the eye-facing concave external surface.

The eyelid occlusion sensor of the eye-mountable ophthalmic device 210 can be operated to output a signal related to a degree of occlusion of the eyelid occlusion sensor and/or of the eye-mountable ophthalmic device 210 by one or both of the eyelids 30, 32 and/or by some other accessory tissue of the eye 10 (e.g., tissues at a corner of the eye 10). Such an output could have a characteristic value (e.g., a characteristic high value) when the eyelids 30, 32 of the eye 10 are open or otherwise minimally occluding the eye-mountable ophthalmic device 210, as shown in FIG. 2A.

Such an output of the eye occlusion sensor could be related to an amount of light received by one or more light-sensitive elements of the eye occlusion sensor, an electrical impedance between two or more electrodes of the eye occlusion sensor that are in contact with a tear film or some other element(s) of the eye 10 or eyelids 30, 32, or some other physical variable related to the degree of occlusion of one or more elements of the device 210. In some examples, the output of the eyelid occlusion sensor could be related to an impedance magnitude, a real impedance, an imaginary impedance, an impedance at two or more frequencies, an inductance, a capacitance, a resistance, a quality factor, a resonance frequency, or some other electrical property of one or more elements of a component (e.g., a conductive loop) of the eyelid occlusion sensor that is inductively, capacitively, or otherwise electrically coupled to tissues (e.g., the eyelids 30, 32) of the eye 10.

Figure 2B:
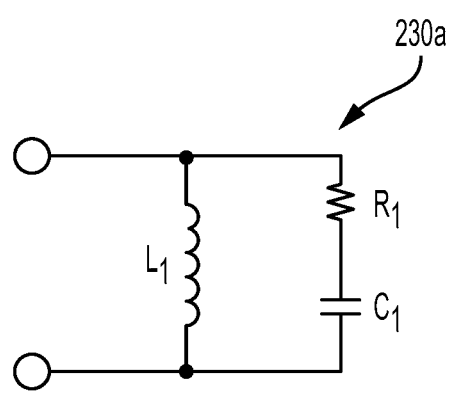
FIG. 2B is an example equivalent electronic circuit of an element of the device shown in FIG. 2A.

For example, the eyelid occlusion sensor could include a conductive loop (e.g., similar to conductive loop 170) that is, when the eye-mountable ophthalmic device 210 is mounted to the eye 10, electrically coupled to tissues of the eye 10 that are proximate to the conductive loop. Such a conductive loop could have electrical characteristics similar to an equivalent circuit comprising one or more inductors, capacitors, and/or resistors, where the properties of one or more of the elements of the equivalent circuit are related to the degree of occlusion of the eye-mountable ophthalmic device 210. FIG. 2B shows an example of such an equivalent circuit 230a corresponding to a conductive loop of the eye-mountable ophthalmic device 210 when the eyelids 30, 32 are open, as shown in FIG. 2A. The equivalent circuit 230a includes an inductor having a first inductance, $L_1$. The inductor is connected in parallel with a resistor and a capacitor that are connected in series. The resistor has a first resistance, $R_1$, and the capacitor has a first capacitance, $C_1$. One or more of the inductance of the inductor, the resistance of the resistor, or the capacitance of the capacitor could be dependent on a degree of occlusion of the device 210 by the eyelids 30, 32 or by some other tissues of or near the eye 10. The change in such properties could be detected, using the eyelid occlusion sensor (e.g., by applying a pulse of voltage or current to the conductive loop and detecting a property of a voltage or current responsively exhibited by the conductive loop), and used to generate the output of the eyelid occlusion sensor that is related to the degree of occlusion of the device 210.

Figure 2C:
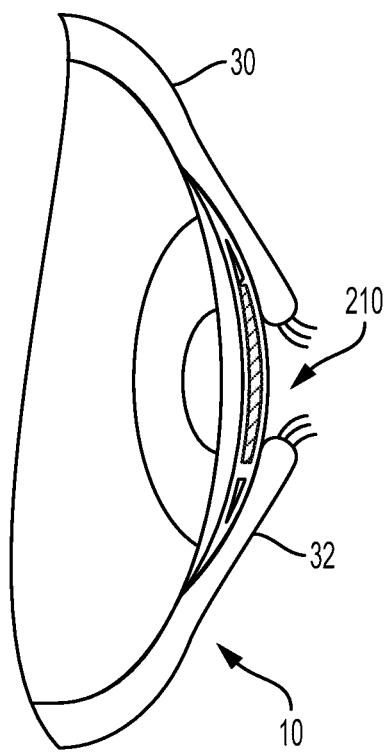
FIG. 2C is a side cross-section view of the example eye-mountable ophthalmic device and eye shown in FIG. 2A but with the eye-mountable ophthalmic device partially occluded by eyelids.
Figure 2D:
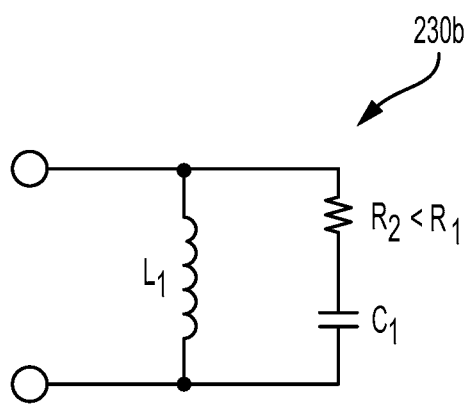
FIG. 2D is an example equivalent electronic circuit of an element of the device shown in FIG. 2C.

Such an increase in occlusion of the eye-mountable ophthalmic device could include the user blinking, squinting, or otherwise moving the eyelids 30, 32 closer together. A squint is illustrated in FIG. 2C, which shows that the upper eyelid 30 has been partially lowered over the eye 10 and the eye-mountable ophthalmic device 210 and the lower eyelid 32 has been partially raised over the eye 10 and the eye-mountable ophthalmic device 210. As a result, the eye-mountable ophthalmic device 210 is partially occluded by the eyelids 30, 32. Correspondingly, the equivalent resistance of the conductive loop could decrease. This is illustrated by FIG. 2D, which shows a second equivalent circuit 230b corresponding to the conductive loop of the eye-mountable ophthalmic device 210 when the eyelids 30, 32 are partially closed, as shown in FIG. 2C. The second equivalent circuit 230b corresponds to the first equivalent circuit 230a except that the resistance of the resistor is $R_2$, which is less than $R_1$.

Figure 2E:
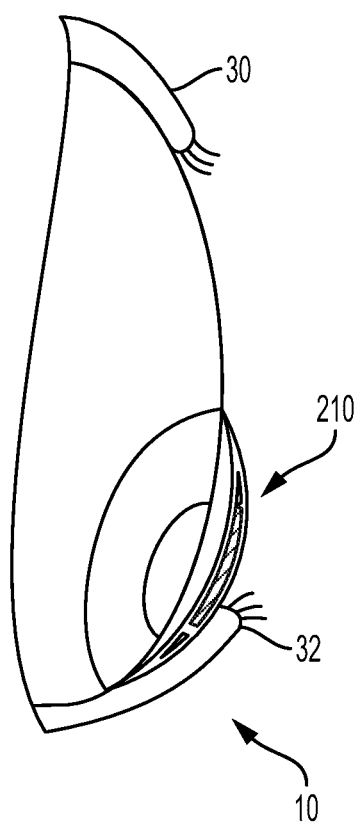
FIG. 2E is a side cross-section view of the example eye-mountable ophthalmic device and eye shown in FIG. 2A but with the eye directed downward such that the eye-mountable ophthalmic device is partially occluded by an eyelid.

Other motions or movements of the eye 10, the eyelids 30, 32 or other tissues of a wearer could result in an increase in the degree of occlusion of the eye-mountable ophthalmic device 210 which could be detected by the eyelid occlusion sensor. For example, the wearer could look downward, upward, or in some other direction such that the eye-mountable ophthalmic device 210 is at least partially occluded by one of the eyelids 30, 32 or by some other tissue of or near the eye 10. A downward look is illustrated in FIG. 2E, which shows that the eye 10 has been rotated to look downward such that the eye-mountable ophthalmic device 210 is partially occluded by the lower eyelid 32. Correspondingly, the equivalent resistance of the conductive loop could decrease, e.g., as illustrated in FIG. 2D.

Such changes in an electrical property of a conductive loop, or of some other component of an eyelid occlusion sensor, could be detected in a variety of ways. In some examples, such detection could include applying a specified voltage and/or current waveform to the conductive loop (or other component of the sensor) and detecting an electrical response (e.g., a voltage across, a current through) of the conductive loop. Such an applied voltage and/or current waveform could include a sinusoidal waveform, a square waveform, or some other repeating waveform having a specified frequency, phase, amplitude, or other properties. An amplitude, relative phase, frequency, or other properties of a corresponding current through and/or voltage across the conductive loop could then be detected (e.g., by detecting the current and/or voltage at one or more points in time) and used to generate an output related to the degree of occlusion of the device 210 (e.g., an output related to the impedance of the conductive loop). In some examples, multiple different sinusoidal or otherwise repeating waveforms could be applied at respective different frequencies, e.g., to determine information related to an impedance spectrum or other electrical characteristics of the conductive loop.

In some examples, the applied voltage and/or current waveform could include one or more pulses (e.g., square pulses) of a specified voltage or current. An amplitude at one or more subsequent points in time or other properties of a corresponding current through and/or voltage across the conductive loop could then be detected (e.g., by detecting the current and/or voltage at one or more points in time) and used to generate an output related to the degree of occlusion of the device 210 (e.g., an output related to a time constant of the decay of the voltage across the conductive loop over time, an output related to the impedance of the conductive loop).

III. Example User Interactions with an Ophthalmic Device

An eye-mountable, implantable, or otherwise configured ophthalmic device as described herein could include an adjustable lens and could operate the adjustable lens to provide a controllable optical power to an eye. Such a controllable optical power could be provided to restore a degree of accommodation to the eye (e.g., a degree of accommodation that has been reduced by age, removal of a crystalline lens of the eye, or due to some other factors) or to provide some other benefit. The optical power of the adjustable lens could be controlled based on a variety of different conditions. In some examples, the ophthalmic device could receive wireless communications (e.g., radio frequency signals, optical signals) from an external device (e.g., a manual control pendant, a device including one or more sensors, an implanted device configured to detect activity of the ciliary muscles of an eye) and operate the adjustable lens based on such communications. Additionally or alternatively, the ophthalmic device could include one or more sensors to detect one or more physical variables that could be used to determine an optical power to provide using the adjustable lens. Such detected physical properties could be related to explicit movements (e.g., eye blinks, squints, eye motions) performed by a wearer to control the ophthalmic device (e.g., according to a specified user interface scheme of the device). Such detected physical properties could additionally or alternatively be related to other movements performed by a wearer, e.g., a downward motion of the eye corresponding to use of near-focus areas of a bifocal lens for reading, a squint indicating effortful viewing of an object.

Such an ophthalmic device could include an eyelid occlusion sensor configured to generate one or more outputs related to a degree of occlusion of the eyelid occlusion sensor and/or of the ophthalmic device by one or more eyelids or other tissues of or near an eye to which the device is mounted and/or in which the device is implanted. By generating an output related to a degree of occlusion of the ophthalmic device, the eyelid occlusion sensor can facilitate control of the adjustable lens based on blinks, squints, downward gazes, or other movements of an eye, eyelids, or other tissues of or near a wearer's eye. Such a range of detectable movements can permit more complex or otherwise improved user interface schemes for the operation of the adjustable lens of the ophthalmic device. For example, such an eyelid occlusion sensor could facilitate a user interface scheme wherein a wearer looking downward, as when using a bifocal lens to view a nearby object, may be detected and used to set or change an optical power provided by the adjustable lens.

Further, detection of partial occlusion of the ophthalmic able device may permit a wearer to receive feedback from the ophthalmic device while operating the device, as the wearer may continue to view his or her environment through the adjustable lens while only partially occluding the ophthalmic device (e.g., by squinting or looking downward). Such feedback could include the wearer sensing that the optical power provided by the adjustable lens has changed.

The output of such an eyelid occlusion sensor could be used in a variety of ways to operate an adjustable lens or to control some other aspect(s) of the operation of an eye-mountable or otherwise configured ophthalmic device. The ophthalmic device could be operated based on a level, an amount of noise, a pattern, one or more edges, or other features or properties of the output of such an eyelid occlusion sensor. The output of such an eyelid occlusion sensor could be used to detect blinks, winks, squints, downward gazes, upward gazes, saccades, or other movements or properties of an eye, one or more eyelids, or of some other tissue(s) of or near an eye.

Figure 3:
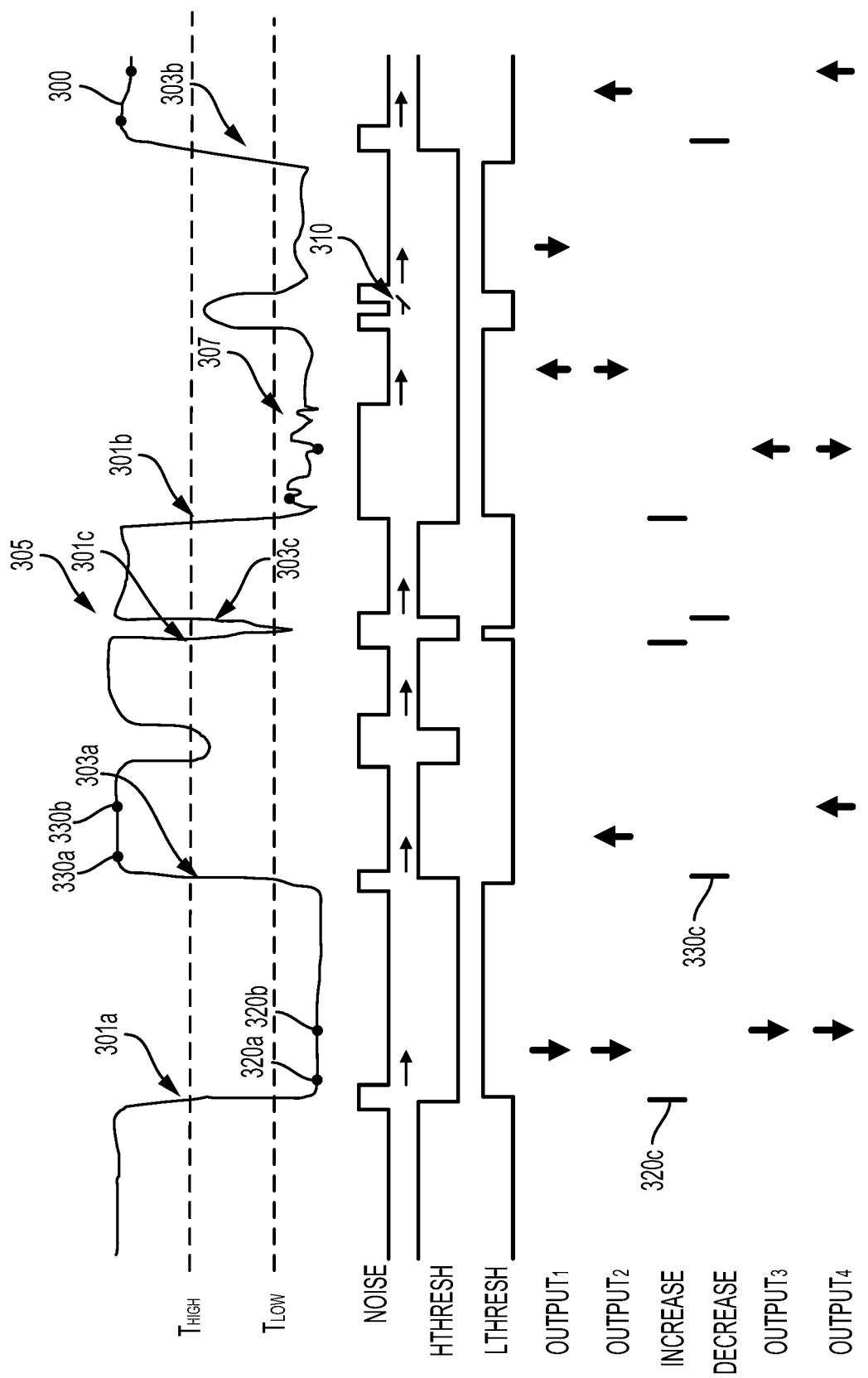
FIG. 3 illustrates an example signal generated using an eyelid occlusion sensor.

FIG. 3 shows an example output 300 generated by an eyelid occlusion sensor as a function of time. The output 300 is related to a degree of occlusion of an eye-mountable ophthalmic device that includes the eyelid collusion sensor, with lower levels of the output 300 indicating greater levels of occlusion of the eye-mountable ophthalmic device. The example output 300 includes a variety of features related to the movement of an eye, eyelids, and/or an environment of the eye-mountable ophthalmic device. For example, the output 300 includes a number of negative edges 301a, 301b, 301c during which the degree of occlusion of the eye-mountable ophthalmic device increased. The output also includes a number of positive edges 303a, 303b, 303c during which the degree of occlusion of the eye-mountable ophthalmic device decreased. Such edges could be related to squints, winks, blinks, downward gazes, or other motions of an eye and/or eyelids. For example, a blink 305 is represented in the output 300 by a negative edge 301c followed by a positive edge 303c. The output 300 also includes noise 307. Such noise could represent movements of the eye and/or eyelids, e.g., one or more saccades. Additionally or alternatively, such noise could represent noise within circuitry of the eyelid occlusion sensor (e.g., due to electromagnetic noise that has coupled into a circuit of the sensor), variation in a property of the environment of a wearer (e.g., a variation in an ambient light level), or some other source of noise.

In order to detect movements of a wearer's eye and/or eyelids that may be used to control the adjustable lens, a variety of features of the output 300 could be detected. Such features could be detected on a continuous bases (e.g., determined at the same rate that the output 300 is sampled, determined by an analog circuit) or at some other rate or timing. Such detected features could include a noise level of the output 300 (e.g., an RMS noise of the output), whether the output exceeds one or more thresholds, whether the output has increased or decreased (e.g., by more than a threshold rate, by more than a threshold amount within a particular period of time), or some other properties of the output 300.

Determination of such features could include detecting an output of an analog circuit, e.g., an analog comparator, an analog filter, an analog differentiator, a sample-and-hold circuit, an analog signal maximum or minimum level detection circuit, a rectifier, an analog RMS noise detection circuit, or some other analog components. Determination of such features could include detecting an output of a digital circuit, e.g., a digital comparator, a digital filter, a digital differentiator, a digital coincidence detector, a digital accumulator, a counter, a register, or some other digital components. Additionally or alternatively, one or more processors configured to execute programs instructions could be used to detect such features, e.g., by using an analog-to-digital converter to sample the output 300 at a plurality of points in time and then performing some operations, based on the program instructions, to detect the features based on the plurality of samples of the output 300. Such program instructions could be stored in a memory of a controller that includes the one or more processors and/or stored in some other non-volatile computer readable medium. Such a controller could additionally or alternatively include the analog and/or digital elements described above, or some other components (e.g., circuitry for operating an adjustable lens and/or eyelid occlusion sensor).

For example, whether a noise level (e.g., an RMS noise) of the output 300 exceeds a specified level could be detected. The output of such a detection is indicated in FIG. 3 as "NOISE". Additionally or alternatively, whether the output 300 exceeds one or more thresholds could be detected. Note that, as used herein, a signal value exceeding a threshold may in include the signal value being greater than or equal to the value of the threshold. Alternatively, the signal value exceeding the threshold may include the signal value being less than or equal to the value of the threshold. For example, whether the output 300 exceeds a first threshold, "$T_{LOW}$", could be detected. The output of such a detection is indicated in FIG. 3 as "$L_{THRESH}$". Additionally or alternatively, whether the output 300 does not exceed a second threshold, "$T_{HIGH}$", could be detected. The output of such a detection is indicated in FIG. 3 as "$H_{THRESH}$".

Whether a degree of occlusion of the eye-mountable ophthalmic device has decreased or increased during a period of time could be detected. This could include detecting positive and/or negative edges within the output 300. The output of such a detection of negative edges is indicated in FIG. 3 as "INCREASE" (as such negative edges may indicate an increase in the degree of occlusion of the eye-mountable ophthalmic device) and the output of such a detection of positive edges is indicated in FIG. 3 as "DECREASE" (as such positive edges may indicate a decrease in the degree of occlusion of the eye-mountable ophthalmic device).

Such detection could be based on the output of a digital or analog differentiator or other filter, a magnitude of change in the output 300 between two different samples of the output 300 (e.g., subsequent samples of the output, subsequent downsampled samples of the output), the contents of a ring buffer or other set of one or more digital registers or sample-and-hold circuits, or some other circuitry or program execution. Such determination could be performed using very little power, e.g., using digital comparators, counters, or other components. Operation of the adjustable lens based on detected edges could be resilient against changes in an average level of the output 300 (e.g., due to changes in an ambient light level, an electrical property of a conductive loop, a hydration level of a wearer) relative to comparison of the output 300 to one or more thresholds, as detection of edges or similar features in the output 300 may be performed based on relative changes in the output 300 rather than based on preset thresholds.

Such detected edges or other features could be used, in an energy-efficient manner, to detect additional features within the output 300. For example, blinks (e.g., 305) could be detected based on proximity in time between a negative edge (e.g., 301c) and a subsequent positive edge (e.g., 303c). Such a detection could be performed in an energy-efficient manner by resetting and/or starting a digital counter in response to detection of a negative edge. Detection of a blink could be based on detection of a positive edge before the digital counter reaches a threshold value. If the counter reaches the threshold value without a positive edge being detected, some operation could be responsively performed (e.g., an operation related to setting or changing an optical power of the adjustable lens).

The features, and methods of detection thereof, described herein could be used according to one or more user interface schemes to control an adjustable lens. Such a user interface scheme could be based on explicit movements that a wearer could perform to control the ophthalmic device (e.g., eye blinks, squints, eye motions). Additionally or alternatively, such a user interface scheme could be based on other movements performed by a wearer, e.g., a downward motion of the eye corresponding to use of near-focus areas of a bifocal lens for reading, a squint indicating effortful viewing of an object.

The ophthalmic device could operate to detect whether the output 300 of the eyelid occlusion sensor is noisy (e.g., due to a user engaging in saccades, blinks, or other transient movements or processes, due to noise present in the circuitry of the eyelid occlusion sensor, or due to optical, electromagnetic, or other noise sources present in the environment of the wearer). Responsive to detecting that the output 300 is not noisy (e.g., that a level of noise in the output 300 during a specified prior period of time was below a specified level), the adjustable lens could be operated based on the magnitude of the output of the eyelid occlusion sensor (e.g., based on a determination that the output 300 does or does not exceed one or more threshold values).

Determining that a level of noise in the output 300 during a specified prior period of time was below a specified level could be performed in an energy-efficient manner by resetting and/or stopping a digital counter in response to detecting that the noise level is above the specified level. Alternatively, such a digital counter could be reset and/or started in response to detecting that the noise level has decreased below the specified level. Detecting that the level of noise during the specified prior period of time was below the specified level could then include determining that the digital counter has reached a specified threshold value. This is illustrated in FIG. 3 with respect to the detected "NOISE" signal by the arrows. Each arrow represents the specified duration of time following a period of time during which the noise in the output 300 was above a specified threshold. At the end of such a duration of time (the heads of the arrows), some operations related to the adjustable lens (e.g., comparison of the level of the output 300 to one or more thresholds) could be performed. Alternatively, if the noise level exceeds the specified threshold value before the counter reaches the threshold, the counter could be reset or some other operation could be performed (illustrated in FIG. 3 by 310).

For example, if output 300 exceeds "$T_{LOW}$" at a first point in time and a level of noise in the output 300 during a specified period of time prior to the first point in time is below the specified level, the optical power of the adjustable lens could be switched between a first optical power and a second optical power. This is indicated in FIG. 3 by "OUTPUT$_1$", with downward arrows indicating setting the optical power of the lens to a first optical power (e.g., an optical power for viewing near objects) and upward arrows indicating setting the optical power of the lens to a second optical power (e.g., an optical power for viewing far objects).

In another example, if output 300 exceeds "$T_{LOW}$" at a first point in time and a level of noise in the output 300 during a specified period of time prior to the first point in time is below the specified level, the optical power of the adjustable lens could be set to a first optical power (e.g., an optical power for viewing near objects). Subsequently, if output 300 does not exceed "$T_{HIGH}$" at a second point in time and a level of noise in the output 300 during a specified period of time prior to the second point in time is below the specified level, the optical power of the adjustable lens could be set to a second optical power (e.g., an optical power for viewing far objects). This is indicated in FIG. 3 by "OUTPUT$_2$", with downward arrows indicating setting the optical power of the lens to the first optical power and upward arrows indicating setting the optical power of the lens to the second optical power. Other methods of operation, based on the illustrated thresholds and/or additional thresholds, could be used. For example, if the level of noise in the output 300 during a specified period of time prior to the first point in time is below the specified level and the output 300 is between two thresholds (e.g., if the output 300 exceeds "$T_{HIGH}$" but does not exceed "$T_{LOW}$"), the optical power of the adjustable lens could be maintained at whatever level it is set to at the first point in time.

The ophthalmic device could operate to detect whether the output 300 of the eyelid occlusion sensor has increased or decreased and, subsequent to such detection, determine whether the output 300 has remained at substantially the same level. Responsive to making such a determination, the adjustable lens could be operated (e.g., based on whether the detected edge was a positive edge or a negative edge, based on whether the detected edge was part of a blink). The device could additionally detect whether the edge was part of a blink (e.g., based on one or more detected subsequent edges) and condition such operations on such a determination.

For example, if a negative edge (e.g., 301a) is detected (e.g. related to the degree of occlusion of the ophthalmic device increasing during a corresponding period of time), the ophthalmic device could determine whether the detected output 300 at a first point in time (e.g., 320a) differs from the detected output 300 at a second subsequent point in time (e.g., 320b) by less than a specified amount. If so, the optical power of the adjustable lens could be switched between a first optical power and a second optical power. The first and second points in time could be points in time specified relative to the timing of the negative edge, e.g., relative to a time of detection of the negative edge (e.g., 320c). This is indicated in FIG. 3 by "OUTPUT$_3$", with downward arrows indicating setting the optical power of the lens to a first optical power (e.g., an optical power for viewing near objects) and upward arrows indicating setting the optical power of the lens to a second optical power (e.g., an optical power for viewing far objects).

In another example, if a negative edge (e.g., 301a) is detected (e.g. related to the degree of occlusion of the ophthalmic device increasing during a corresponding period of time), the ophthalmic device could determine whether the detected output 300 at a first point in time (e.g., 320a) differs from the detected output 300 at a second subsequent point in time (e.g., 320b) by less than a specified amount. If so, the optical power of the adjustable lens could be set to a first optical power (e.g., an optical power for viewing near objects). The first and second points in time could be points in time specified relative to the timing of the negative edge, e.g., relative to a time of detection of the negative edge (e.g., 320c).

Subsequently, if a positive edge (e.g., 303a) is detected (e.g. related to the degree of occlusion of the ophthalmic device decreasing during a corresponding period of time), the ophthalmic device could determine whether the detected output 300 at a third point in time (e.g., 330a) differs from the detected output 300 at a fourth subsequent point in time (e.g., 330b) by less than a specified amount. If so, the optical power of the adjustable lens could be set to a second optical power (e.g., an optical power for viewing far objects). The third and fourth points in time could be points in time specified relative to the timing of the positive edge, e.g., relative to a time of detection of the positive edge (e.g., 330c). This is indicated in FIG. 3 by "OUTPUT$_4$", with downward arrows indicating setting the optical power of the lens to the first optical power and upward arrows indicating setting the optical power of the lens to the second optical power.

In some examples, a user interface scheme could include detecting whether a specified number (e.g., three) of one or more events (e.g., blinks) have occurred within a specified span of time. It could also be advantageous to prevent each event that occurs subsequent to such a detection to also trigger such a detection. An ophthalmic device could be configured to perform such operations efficiently by using a number of digital counters, where the number of digital counters is at least twice the number of events to be detected within the specified span of time. Upon detection of an event, a first digital counter could be started (e.g., incremented during each of a number of subsequent sample periods or other clock periods) and a second digital counter could be incremented. If the event is detected again before the first counter reaches a specified threshold, a third digital counter could be started, the first digital counter could be incremented, and a fourth digital counter could be incremented. The specified threshold corresponds to the specified span of time. Upon detection of further events before the first counter reaches the specified threshold, a further digital counter could be started, a yet further digital counter could be incremented, and the even-numbered counters could be incremented. If the second digital counter reaches the number of events to be detected before the first digital counter reaches the specified threshold, the ophthalmic device could detect that the specified number (e.g., three) of one or more events (e.g., blinks) has occurred within the specified span of time. Additionally, the digital counters could be reset and/or stopped. Alternatively, if the first digital counter reaches the specified threshold without the second digital counter reaching the number of events to be detected, the digital counters could be reset and/or stopped.

Figure 4:
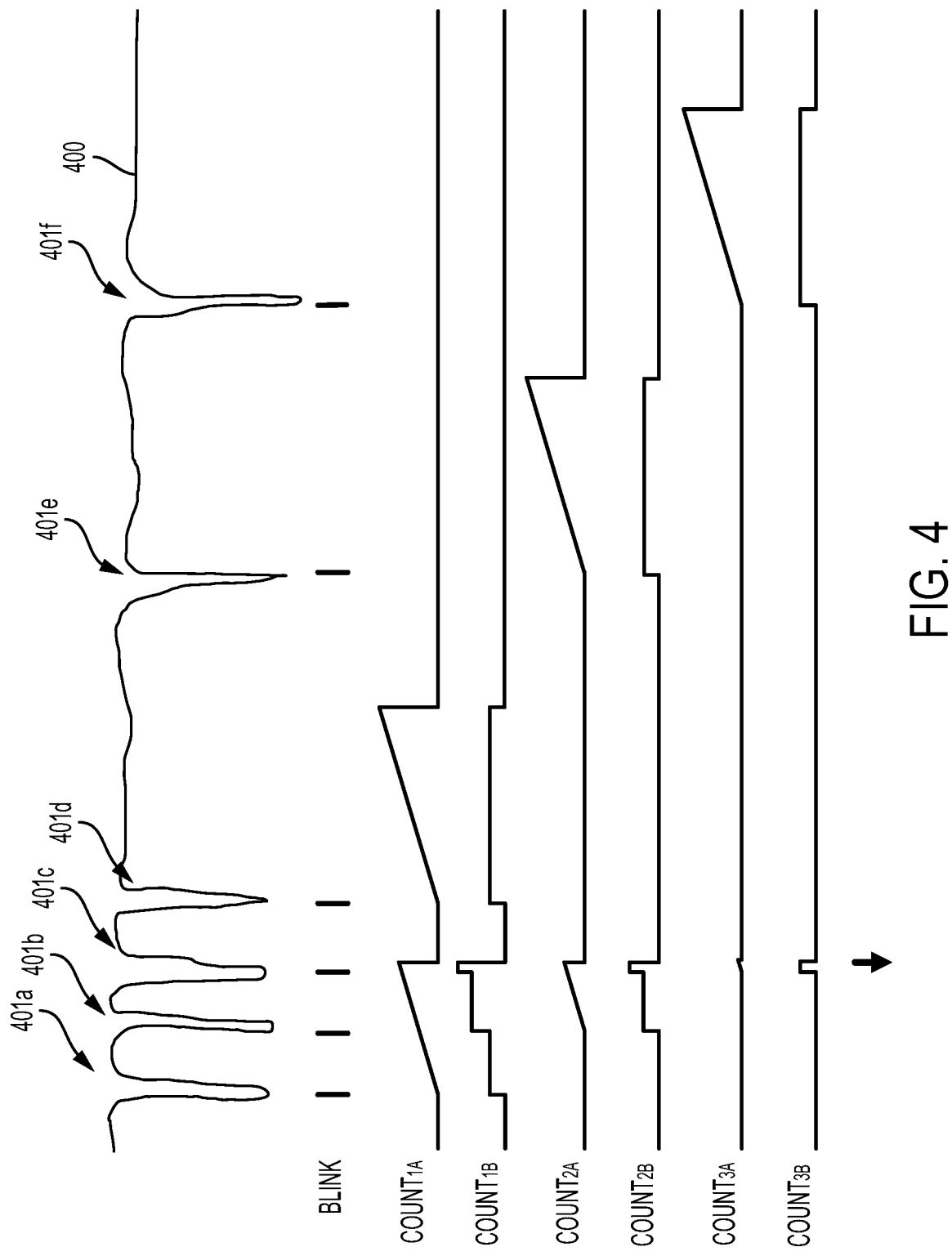
FIG. 4 illustrates an example signal generated using an eyelid occlusion sensor.

An example scenario for using counters is illustrated in FIG. 4, which shows an example output 400 generated by an eyelid occlusion sensor. The example output 300 includes a variety of features related to the movement of an eye, eyelids, and/or an environment of the ophthalmic device. As shown, the output 400 represents a number of blinks 401a, 401b, 401c, 401d, 401e, 401f. The timing of detection of the blinks 401a, 401b, 401c, 401d, 401e, 401f is represented in FIG. 4 by "BLINKS". FIG. 4 also represents the value of six different digital counters of the ophthalmic device over time (represented by "COUNT$_{1A}$", "COUNT$_{1B}$", "COUNT$_{2A}$", "COUNT$_{2B}$", "COUNT$_{3A}$", and "COUNT$_{3B}$"). The ophthalmic device is configured to detect whether three blinks have occurred within a specified span of time.

Upon detection of the first blink 401a, the first counter ("COUNT$_{1A}$") is started and the second counter ("COUNT$_{1B}$") is incremented. Upon detection of the second blink 401b, the third counter ("COUNT$_{2A}$") is started and the first counter and the third counter ("COUNT$_{2B}$") are incremented. Upon detection of the third blink 401c, the fifth counter ("COUNT$_{3A}$") is started and the first counter, the third counter, and the sixth counter ("COUNT$_{3B}$") are incremented. The ophthalmic device then detects that the second counter has reached the threshold number of events, three, and responsively determines that three blinks have occurred within the specified span of time (represented in FIG. 4 by the arrow). The ophthalmic device also resets and stops the digital counters. Subsequently, the fourth blink 401d is detected and, responsive to that detection, the first counter ("COUNT$_{1A}$") is started and the second counter ("COUNT$_{1B}$") is incremented. However, no further events are detected before the first counter reaches a threshold value related to the specified span of time, so the first and second counters are stopped and reset.

The systems and methods described herein could be operated to detect blinks, winks, squints, downward gazes, or other movements of an eye and/or eyelid while detecting a degree of occlusion of the eye (e.g., by detecting an output of an eyelid occlusion sensor) at a low rate, e.g., at a rate that is less than 40 Hertz, or a rate that is less than 20 Hertz. Operating an eyelid occlusion sensor to detect the degree of occlusion of an eye and/or to perform some operations based on the detected degree of occlusion at such a low rate could facilitate the performance of such operations while using a low amount of power, e.g., less than 15 nanoamps, or less than 10 nanoamps. Such low-power operation could allow an ophthalmic device to operate for an extended period of time (e.g., days, weeks) without recharging a rechargeable battery of the ophthalmic device and/or replacing the ophthalmic device.

IV. Example Electronics of an Ophthalmic Device

Figure 5:
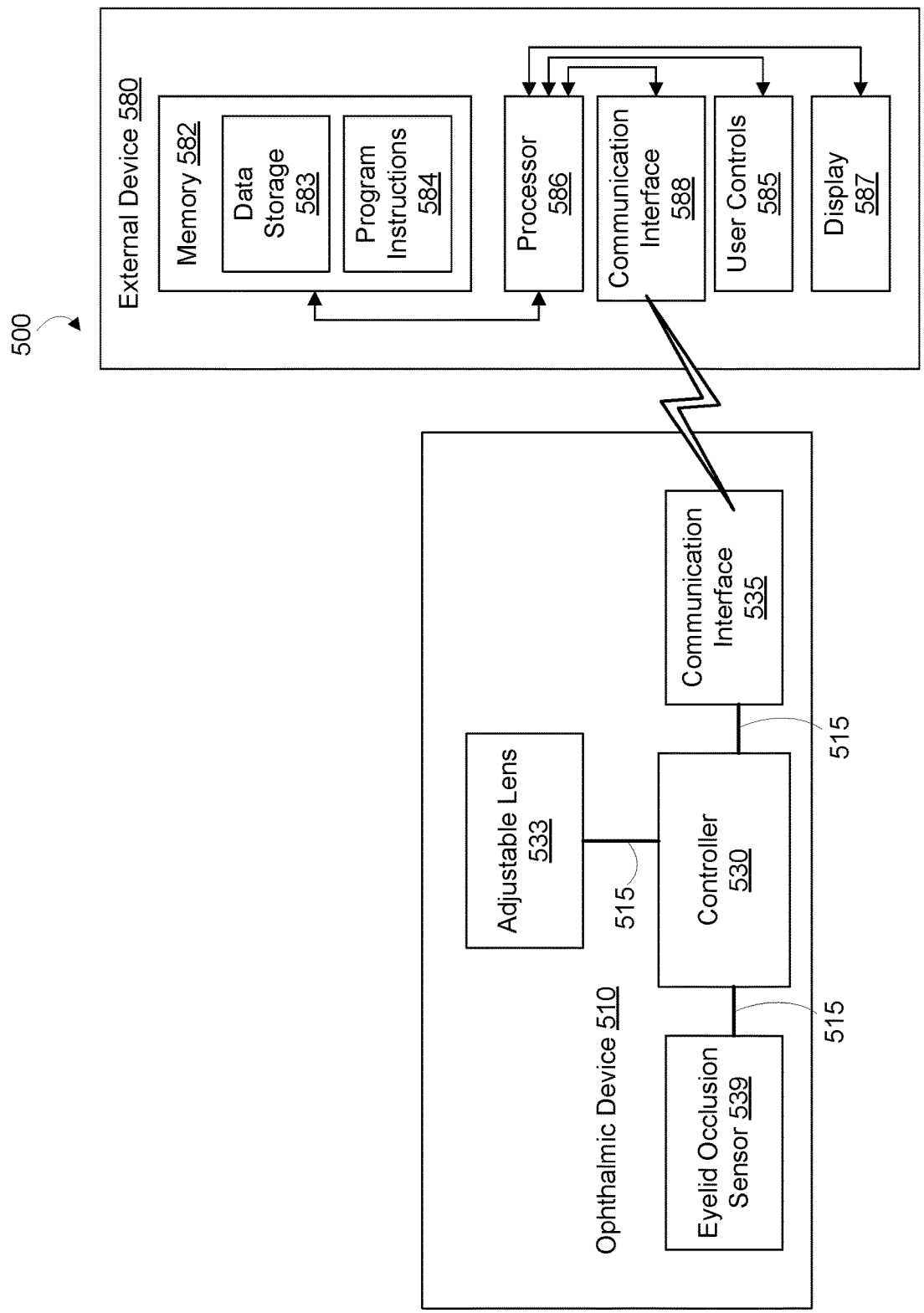
FIG. 5 is a block diagram of an example system that includes an ophthalmic device in wireless communication with an external reader.

FIG. 5 is a block diagram of a system 500 that includes an ophthalmic device 510 (e.g., an eye-mountable device, an eye-implantable device) as described herein. The ophthalmic device 510 is in wireless communication with an external device 580. The ophthalmic device 510 includes a controller 530, an adjustable lens 533, an eyelid occlusion sensor 539, and a communication interface 535. The adjustable lens 533 is configured to provide a controllable optical power, e.g., to an eye to which the ophthalmic device is mounted or in which the ophthalmic device is implanted. The eyelid occlusion sensor 539 is configured to detect occlusion of the sensor 539 and/or the ophthalmic device 510 by one or more eyelids or other tissues proximate to an eye to which the ophthalmic device 510 is mounted, in which the ophthalmic device 510 is implanted, or with which the ophthalmic device 510 is otherwise associated. The adjustable lens 533 and eyelid occlusion sensor 539 are operated by the controller 530. The communication interface 535 includes one or more antennas, amplifiers, oscillators, mixers, modulators, or other elements that can be operated by the controller 530 to wirelessly communicate information between the ophthalmic device 510 and the external device 580 via radio frequency signals or some other wireless signals.

The communication interface 535, the controller 530, the eyelid occlusion sensor 539, and the adjustable lens 533 can all be connected together via interconnects 515, e.g., via patterns metallic traces formed on a substrate material on which the components (e.g., 533, 530, 539, 535) are disposed. Further, impedance sensing electrodes, electrowetting lens electrodes, liquid crystal lens electrodes, conductive loops, antennas, or other elements of the components (e.g., 533, 530, 539, 535) could comprise metallic traces or patterns formed on such a substrate material.

In some examples, one or more components of the ophthalmic device 510 could form part of two or more of the adjustable lens 533, the eyelid occlusion sensor 539, or the communication interface 535. For example, a conductive loop could be used, as part of the eyelid occlusion sensor 539, to detect a degree of occlusion of the ophthalmic device 510 by an eyelid. Such a conductive loop could also be used, as part of the communication interface 535, to send or receive wireless communication signals and/or to receive wireless power from the external device 580.

To facilitate contact-mounting to an eye, a polymeric material of the ophthalmic device 510 can have a concave surface configured to adhere ("mount") to a moistened corneal surface (e.g., by capillary forces with a tear film coating the corneal surface). Additionally or alternatively, the ophthalmic device 510 can be adhered by a vacuum force between the corneal surface and the polymeric material due to the concave curvature. While mounted with the concave surface against the eye, the outward-facing surface of the polymeric material can have a convex curvature that is formed to not interfere with eye-lid motion while the ophthalmic device 510 is mounted to the eye. For example, the polymeric material can be a substantially transparent curved polymeric disk shaped similarly to a contact lens.

The ophthalmic device 510 could be powered in a variety of ways. For example, the ophthalmic device 510 could include an electrochemical battery and/or ultracapacitor to store energy for use by the device 510. Additionally or alternatively, the device 510 could include means for harvesting wireless energy (e.g., radio frequency energy, optical energy). For example, a radio-frequency energy-harvesting antenna (e.g., an antenna of the communication interface 535) can capture energy from incident radio radiation. In another example, a photovoltaic cell or other optical energy receiving element(s) could receive energy from the ambient illumination present in the environment of the device 510 and/or optical energy emitted from an external device (e.g., from the external device 580).

The controller 530 could include a variety of electronic components to facilitate operations of the ophthalmic device 510 as described elsewhere herein. For example, the controller could include amplifier, comparators, sample-and-hold circuitry, analog-to-digital converter(s), voltage references, constant current sources, pulse generators, oscillators, rectifiers, or other circuitry to operate the eyelid occlusion sensor 539 to generate an output related to a degree of occlusion of the eyelid occlusion sensor 539 and/or the ophthalmic device 510 by one or more eyelids or other tissues proximate to an eye with which the ophthalmic device 510 is associated (e.g., to which the device is mounted, in which the device is implanted). The controller 530 could include amplifiers, charge pumps, boost converters, constant current sources, voltage references, switches, blocking capacitors, rectifiers, digital-to-analog converters, or other circuitry to operate the adjustable lens 533 to provide a specified optical power, e.g., to provide an optical power selected from a set of two or more different optical powers. Such different optical powers could facilitate a wearer viewing objects within respective different ranges of distances from the viewer's eye. For example, the adjustable lens 533 could be operated to provide an optical power selected from a two different optical powers, a first optical power corresponding to near vision and a second optical power corresponding to far vision.

The controller 530 could additionally include logic components configured to implement the methods of operation of an ophthalmic device described herein. In some examples, such logic components could include one or more digital counters, clocks, latches, flip-flops, comparators, lookup tables, multipliers, adders, coincidence detectors, registers, or other components configured to provide a finite state machine or other form of digital controller configured to implement the operations described herein. Additionally or alternatively, the controller 530 could include a computing device that includes one or more processors configured to execute program instructions stored in a memory of the device in order to perform the operations described herein. For example, the controller could include a flash memory, a programmable read-only memory, or some other non-volatile computer readable medium that could contain such program instructions. In some examples, the controller 530 could be configured and/or programmed to receive such instructions (e.g., from the external device 580) using the communication interface (e.g., to receive initial programming for the device 510, to receive programming updates, to receive user preferences or parameters).

It is noted that the block diagram shown in FIG. 5 is described in connection with functional modules for convenience in description. However, embodiments of the ophthalmic device 510 can be arranged with one or more of the functional modules ("sub-systems") implemented in a single chip, integrated circuit (e.g., an application-specific integrated circuit), and/or physical feature. That is, the functional blocks in FIG. 5 need not be implemented as separated modules. Moreover, one or more of the functional modules described in FIG. 5 can be implemented by separately packaged chips electrically connected to one another. Further, note that an ophthalmic device as described herein could include additional, fewer, and/or or alternative components to those shown in FIG. 5 (e.g., additional sensors, electrodes, batteries, controllers, transmitters, receivers, light emitters, etc.). For example, the ophthalmic device 510 could lack the communication interface 535 and could be configured to operate independent of any external devices (e.g., 580) to operate the eyelid occlusion sensor 539 and adjustable lens 533 as described herein.

The external device 580 includes a communication interface 588 to send and receive wireless signals to and from the ophthalmic device 510. The external device 580 also includes a computing system with a processor 586 in communication with a memory 582. The external device 580 can also include one or more of user controls 585, and a display 587. The memory 582 is a non-transitory computer-readable medium that can include, without limitation, magnetic disks, optical disks, organic memory, and/or any other volatile (e.g. RAM) or non-volatile (e.g. ROM) storage system readable by the processor 586. The memory 582 can include a data storage 583 to store indications of data, such as user preferences (e.g., a user selection between a number of different potential user interface schemes that could be implemented by the device 510), program settings (e.g., to adjust behavior of the ophthalmic device 510 and/or external device 580), etc. The memory 582 can also include program instructions 584 for execution by the processor 586 to cause the external device 580 to perform processes specified by the instructions 584. For example, the program instructions 584 can cause external device 580 to perform any of the function described herein. For example, program instructions 584 may cause the external device 580 to provide a user interface that allows for retrieving information communicated from the ophthalmic device 510 (e.g., sensor outputs or other information related to the eyelid occlusion sensor 539) by displaying that information on the display 587 in response to commands input through the user controls 585.

The external device 580 can be a smart phone, digital assistant, or other portable computing device with radios, light emitters, light detectors, or other wireless connectivity sufficient to provide for wireless communication with the communication interface 535 of the ophthalmic device 510. The external device 580 can also be implemented as an wireless module (e.g., a radio, an optical data link) that can be plugged into a portable computing device, such as in an example where radio frequency wireless signals used to communicate with the ophthalmic device 510 are at carrier frequencies not commonly employed in portable computing devices. In some instances, the external device 580 is a special-purpose device configured to be disposed relatively near a mounting location of the ophthalmic device 510 on the wearer's body (e.g., near a wearer's eye) to allow the communication interfaces 535, 588 to operate with a low power budget. The external device 580 could also be implemented in eye glasses or a head-mounted display.

V. Example Methods

Figure 6:
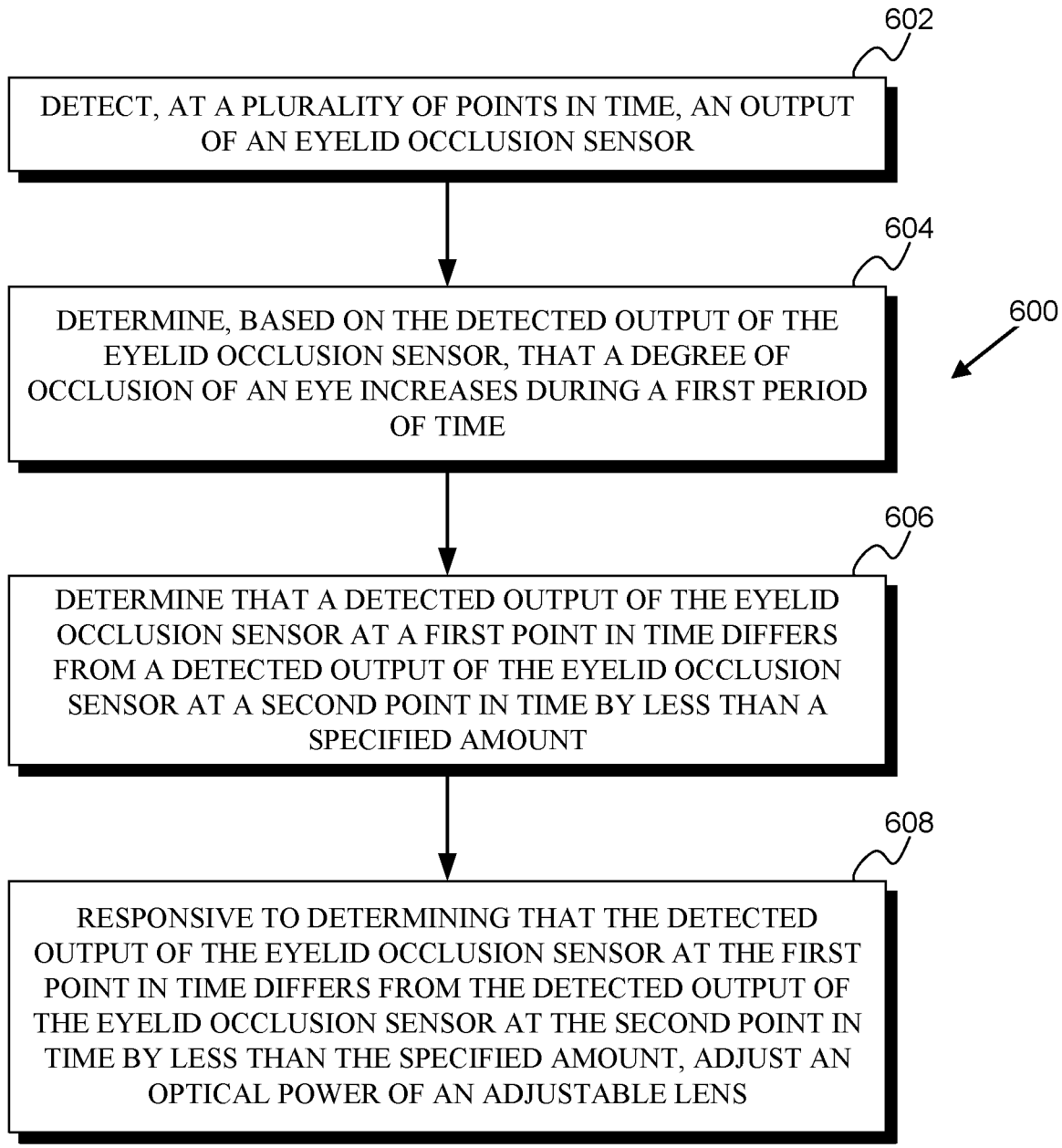
FIG. 6 is a flowchart of an example method.

FIG. 6 is a flowchart of a method 600 for operating an ophthalmic device. The ophthalmic device includes an eyelid occlusion sensor, an adjustable lens, and a controller. The method 600 includes detecting, at a plurality of points in time, an output of the eyelid occlusion sensor (602). This could include applying a specified current and/or voltage waveform to a conductive loop, a light-sensitive element (e.g., a photodiode), two or more electrodes, or some other element(s) of the eyelid occlusion sensor at each of the plurality of points in time. Detecting the output of the eyelid occlusion sensor could include operating an ADC, a comparator, or some other electronic component to detect a voltage across and/or a current through an element (e.g., a conductive loop, a light-sensitive element, two or more electrodes) of the eyelid occlusion sensor one or more times for each of the plurality of points in time. Detecting the output of the eyelid occlusion sensor could include using an analog or digital filter, comparator, sample-and-hold, RMS detector, coincidence detector, or some other electronic component to generate a signal (e.g., an analog signal, a digital signal) related to the output of the eyelid occlusion sensor.

The method 600 includes determining, based on the detected output of the eyelid occlusion sensor, that a degree of occlusion of an eye increases during a first period of time (604). This could include this could include detecting positive and/or negative edges or other features within the detected output. Such detection could be based on the output of a digital or analog differentiator or other filter, a magnitude of change in the output between two different samples of the output (e.g., subsequent samples of the output, subsequent downsampled samples of the output), the contents of a ring buffer or other set of one or more digital registers or sample-and-hold circuits, or some other circuitry or program execution.

The method 600 includes determining that a detected output of the eyelid occlusion sensor at a first point in time differs from a detected output of the eyelid occlusion sensor at a second point in time by less than a specified amount, wherein the second point in time is after the first period of time (606). This could include determining that a difference between the detected output of the eyelid occlusion sensor at the first point and the detected output of the eyelid occlusion sensor at the second point in time is less than a specified value. The first and second points in time could be points in time specified relative to the timing of the detected edge or relative to some other time related to the first period of time during which the degree of occlusion of the eye increased.

The method 600 includes, responsive to determining that the detected output of the eyelid occlusion sensor at the first point in time differs from the detected output of the eyelid occlusion sensor at the second point in time by less than the specified amount, adjusting an optical power of the adjustable lens (608). This could include setting the adjustable lens to a first optical power (e.g., an optical power for viewing near objects), switching the adjustable lens between a first optical power (e.g., an optical power for viewing near objects) and a second optical power (e.g., an optical power for viewing far objects), or performing some other operations. Such a determination could be based on some other determinations, e.g., a determination that the first period of time, during which the degree of occlusion of the eye increased, was not followed, within a specified minimum period of time, by a second period of time during which the degree of occlusion of the eye decreased.

The method 600 could include additional steps or elements in addition to those depicted in FIG. 6 (i.e., 602, 604, 606, 608). The method 600 could include other steps or elements as described elsewhere herein, or some further steps or elements.

Figure 7:
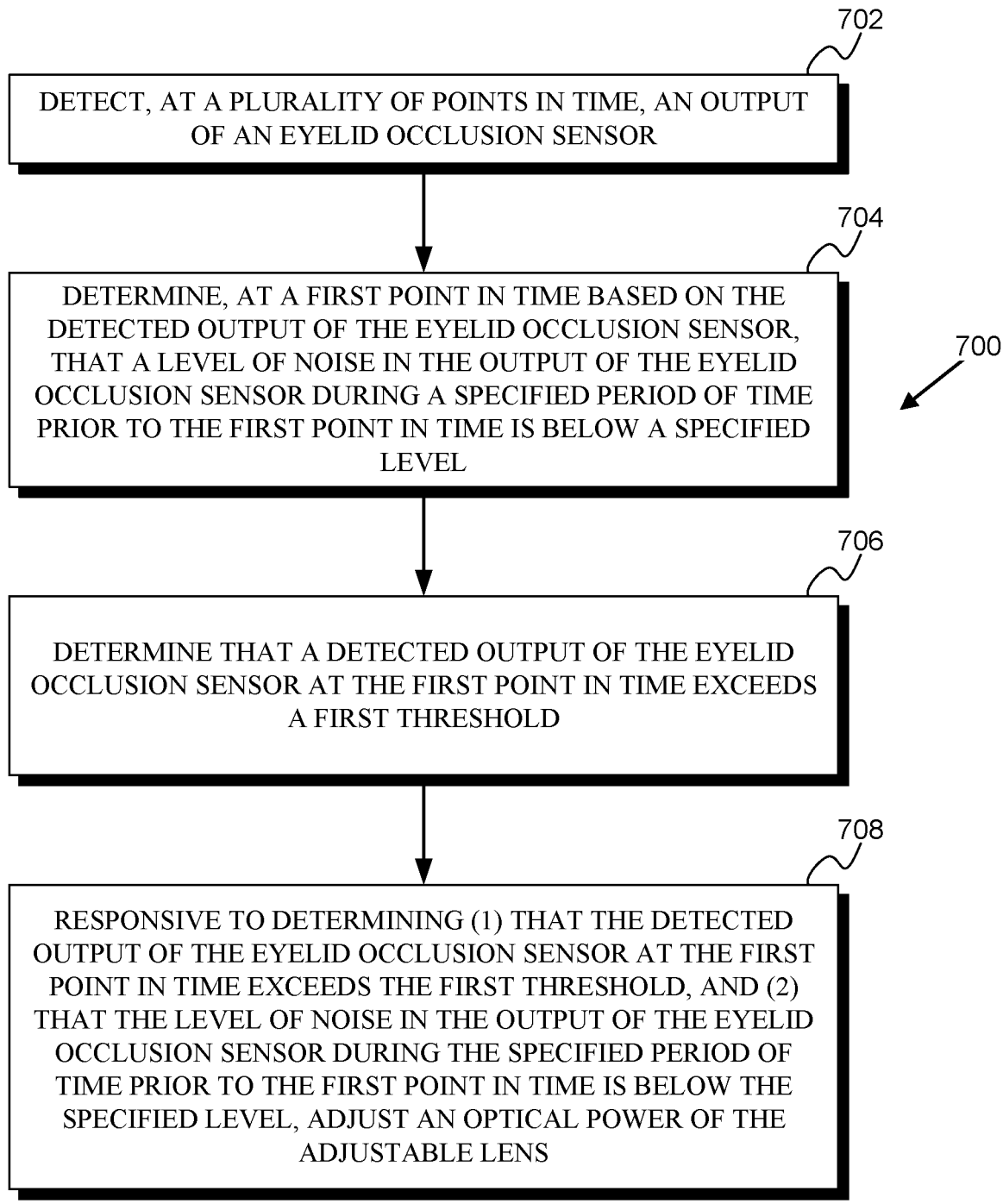
FIG. 7 is a flowchart of an example method.

FIG. 7 is a flowchart of a method 700 for operating an ophthalmic device. The ophthalmic device includes an eyelid occlusion sensor, an adjustable lens, and a controller. The method 700 includes detecting, at a plurality of points in time, an output of the eyelid occlusion sensor (702). This could include applying a specified current and/or voltage waveform to a conductive loop, a light-sensitive element (e.g., a photodiode), two or more electrodes, or some other element(s) of the eyelid occlusion sensor at each of the plurality of points in time. Detecting the output of the eyelid occlusion sensor could include operating an ADC, a comparator, or some other electronic component to detect a voltage across and/or a current through an element (e.g., a conductive loop, a light-sensitive element, two or more electrodes) of the eyelid occlusion sensor one or more times for each of the plurality of points in time. Detecting the output of the eyelid occlusion sensor could include using an analog or digital filter, comparator, sample-and-hold, RMS detector, coincidence detector, or some other electronic component to generate a signal (e.g., an analog signal, a digital signal) related to the output of the eyelid occlusion sensor.

The method 700 includes determining, at a first point in time based on the detected output of the eyelid occlusion sensor, that a level of noise in the output of the eyelid occlusion sensor during a specified period of time prior to the first point in time is below a specified level (704). This could include resetting and/or stopping a digital counter in response to detecting that the noise level is above the specified level. Alternatively, such a digital counter could be reset and/or started in response to detecting that the noise level has decreased below the specified level. Detecting that the level of noise during the specified prior period of time was below the specified level could then include determining that the digital counter has reached a specified threshold value.

The method 700 includes determining that a detected output of the eyelid occlusion sensor at the first point in time exceeds a first threshold (706). This could include operating an analog or digital comparator to determine that the output of the eyelid occlusion sensor exceeds the first threshold. The method 700 also includes, responsive to determining (1) that the detected output of the eyelid occlusion sensor at the first point in time exceeds the first threshold, and (2) that the level of noise in the output of the eyelid occlusion sensor during the specified period of time prior to the first point in time is below the specified level, adjusting an optical power of the adjustable lens (708). This could include setting the adjustable lens to a first optical power (e.g., an optical power for viewing near objects), switching the adjustable lens between a first optical power (e.g., an optical power for viewing near objects) and a second optical power (e.g., an optical power for viewing far objects), or performing some other operations.

The method 700 could include additional steps or elements in addition to those depicted in FIG. 7 (i.e., 702, 704, 706, 708). The method 700 could include other steps or elements as described elsewhere herein, or some further steps or elements.

VI. Example Synchronization of Ophthalmic Devices

Devices as described herein may be used in pairs, e.g., with an individual device mounted to and/or implanted within each of a user's eyes. Each device of such a pair can operate to detect eye-based gestures of their respective eyes (e.g., by detecting the level of occlusion of a sensor of the device over time) and, responsive to detecting such gestures, adjust the optical power provided by respective adjustable lenses of the devices. Each device of such a pair could perform such operations substantially independently (e.g., without engaging in communication with each other) to compare sensor outputs, to synchronize operation of the adjustable lenses (e.g., to maintain the adjustable lenses at the same level of optical power), or to perform some other operations in concert.

However, when two devices (e.g., eye-mountable devices, eye-implanted devices) are operated in such a manner, their operations may become unsynchronized. For example, a device mounted to the left eye of a wearer could provide an optical power suited to distance vision while a device mounted to the right eye of the wearer could provide an optical power suited to close-up vision. Such desynchronization may occur due to one of the devices failing to detect an eye-based gesture (a false negative detection), one of the devices erroneously detecting an eye-based gesture when none occurred (a false positive detection), or due to some other circumstance. Such circumstances could be related to differences in anatomy or physiology between the eyes, to differences in the electrical or other properties of the devices, to differences in the ambient lighting or other properties of the environment of the devices, or to some other factors.

In order to prevent such desynchronized operation and/or to provide other benefits, the devices could be provided with means for wireless communication. However, such means could increase the cost of the devices, impose additional size, aesthetic, or volume constraints on the devices, or could be associated with some other unwanted structural or functional modification to the devices. Further, operating such means to communicate wirelessly may require more energy than is feasible, given a particular device power budget.

Alternatively, devices as described herein could be operated to detect multiple different eye-based gestures, where at least one of the detected gestures is a "reset" gesture. Such a reset gesture could provide a failsafe method for the ophthalmic devices to be placed into a specified, synchronized operational state. Such a "reset state" could include adjusting the adjustable lens of an ophthalmic device to a specified "reset" optical power (e.g., an optical power suited for distance vision) or setting some other operational state, parameter, or mode of the ophthalmic device to a pre-specified state. If a wearer determines that a pair of devices in use by the wearer has become desynchronized, the wearer can perform the "reset" gesture in order to place the devices back into synchronized operation.

Such "reset" gestures may generally have longer durations, require more eye-based activity, or be otherwise more effortful to perform than other gestures detected by devices described herein that are used by such devices to perform non-"reset" operations (e.g., to adjust an optical power of an adjustable lens between two different optical powers suited to distance vision and close-up vision, respectively). For example, a "reset" gesture could include more sub-gestures (e.g., blinks, winks, squints, downward glances), longer duration sub-gestures (e.g., longer-duration winks, squints, etc.), longer overall duration, a more complicated sequence of sub-gestures (e.g., a specific alternating sequence of winks and blinks), or could require more effort, on the part of a wearer, to perform than other non-"reset" gestures. Such differences between "reset" gestures and other gestures may provide for easier control of non-"reset" operations of the device (e.g., to adjust the optical power of a device between distance vision and close-up vision), may prevent inadvertent activation of the "reset" operation of the device (which is likely to be needed only rarely), and/or may provide other benefits.

Figure 8B:
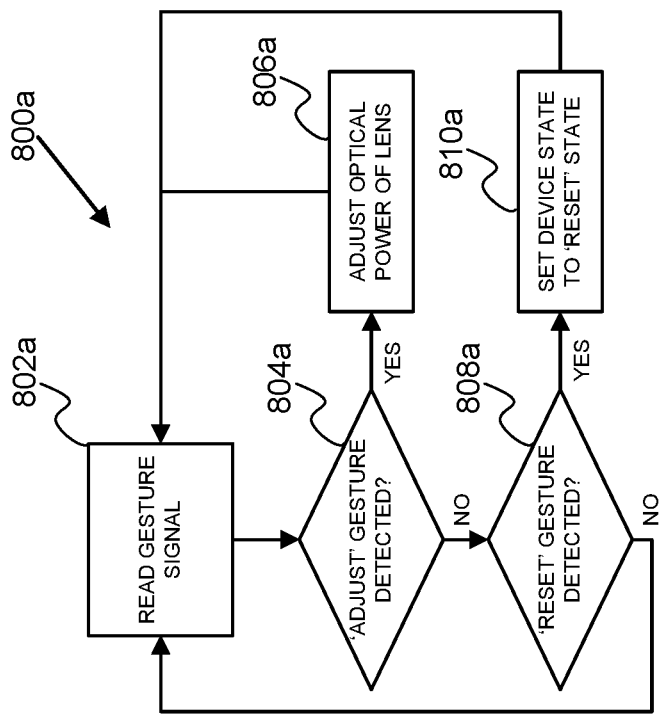
FIG. 8B is a flowchart of an example method.
Figure 8A:
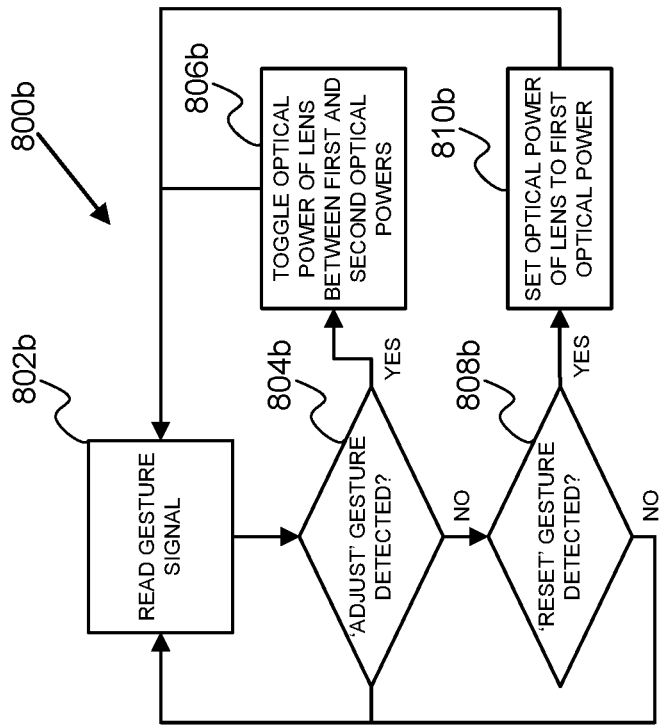
FIG. 8A is a flowchart of an example method.

FIG. 8A is a flowchart of a method 800A for operating an ophthalmic device as described herein. The method 800A includes reading a gesture signal 802a. This could include detecting, at a plurality of points in time, an output of an eyelid occlusion sensor or detecting the output of some other sensor in some other manner. For example, digital and/or analog circuitry could receive a signal from a sensor (e.g., an eyelid occlusion sensor) and produce an output (e.g., a digital output) when the sensor output is indicative of a gesture. The method 800a also includes determining, based on the gesture signal, whether an "adjust" gesture is present in the gesture signal 804a. If such an "adjust" gesture is detected, the optical power of an adjustable lens of the device is adjusted 806a (e.g., toggled between first and second optical powers, set to a particular optical power corresponding to the detected "adjust" gesture). If an "adjust" gesture is not detected, the method 800a includes determining, based on the gesture signal, whether a "reset" gesture is present in the gesture signal 808a. If such a "reset" gesture is detected, the device is set into a "reset" state 810a. This could include adjusting the optical power of the adjustable lens to a pre-specified "reset" optical power, setting an operational mode of the device to a pre-specified "reset" mode, or performing some other operations to "reset" the device.

The "adjust" gesture(s) detected in FIG. 8A could be any of the eye-based gestures described herein. For example, the "adjust gesture could include one or more blinks, winks, squints, downward gazes, or other eye-related activities or combinations or permutations thereof. Detecting an "adjust" gesture 804a could include detecting one of a set of "adjust" gestures. For example, there could be first and second "adjust" gestures corresponding to respective first and second optical powers of the adjustable lens (e.g., a distance-vision power and a close-up vision power) and detecting a particular one of the multiple "adjust" gestures could result in the device adjusting the optical power of the lens to the optical power corresponding to the detecting one of the "adjust" gestures. The "adjust" gesture(s) could be detected according to any of the methods described herein. For example, detecting an "adjust" gesture could include determining a level of noise present in the gesture signal, comparing the gesture signal at one or more points in time to itself and/or one or more threshold levels, determining whether the gesture signal has increased or decreased over time, or determining some other features or properties of the gesture signal.

The "reset" gesture(s) detected in FIG. 8A could be any of the eye-based gestures described herein. In some examples, the "reset" gesture could have a greater duration, include more sub-gestures (e.g., more blinks), include a more complicated sequence of sub-gestures, include longer-duration sub-gestures (e.g., longer duration squints), or otherwise require more effort and/or time to accomplish than the "adjust" gesture(s). In some examples, the "reset" gesture could include the "adjust" gesture as a sub-gesture. For example, the "adjust" gesture could include performing, e.g., three blinks in succession within a specified period of time without performing any additional blinks within another specified period of time thereafter. The "reset" gesture could, in such an example, include performing more than three blinks in succession within yet another specified period of time.

Setting the device to a "reset state" 810a could include adjusting an adjustable optic to a pre-specified optical power, setting an internal state or mode of the device to a pre-specified state or mode, resetting one or more setting or states (e.g., threshold values) of the device to a factory standard settings, or operating the device in some other fashion such that, after setting the device to the "reset state," the device operates in a pre-specified manner. In some examples, this could include setting the device to a "reset state" that is in-common with the "reset state" of a paired device. For example, the "reset state" for both of the pair of devices could include the adjustable lens of each device being set to the same optical power to facilitate distance vision. Alternatively, the "reset state" for each device of a pair of devices could differ, e.g., according to differences in the prescription of each eye of a wearer. For example, the "reset state" for a first device could include the adjustable lens of the first device being set to a first prescribed optical power to facilitate distance vision in the left eye of a wearer, while the "reset state" for a second device could include the adjustable lens of the second device being set to a second prescribed optical power to facilitate distance vision in the right eye of a wearer.

In some examples, setting a device to a "reset state" could include operating the adjustable lens of the device to provide a pre-specified optical power or to assume some other pre-specified state. This could be especially beneficial in examples where other eye-based gestures detected by the device (e.g., squints, winks, downward glances) are used to toggle the optical power of the adjustable lens between two or more discrete, pre-specified optical powers (e.g., between a first optical power suited to distance vision and a second optical power suited to close-up vision). FIG. 8B is a flowchart of such a method 800b for operating an ophthalmic device as described herein.

The method 800b includes reading a gesture signal 802a. The method 800b also includes determining, based on the gesture signal, whether an "adjust" gesture is present in the gesture signal 804b. If such an "adjust" gesture is detected, the optical power of an adjustable lens of the device is toggled between first and second optical powers 806b. If an "adjust" gesture is not detected, the method 800b includes determining, based on the gesture signal, whether a "reset" gesture is present in the gesture signal 808b. If such a "reset" gesture is detected, the optical power of the adjustable lens is set to the first optical power 810b.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An ophthalmic device comprising:
   an eyelid occlusion sensor;
   an adjustable lens; and
   a controller, wherein the controller comprises electronics that perform operations comprising:
      detecting, at a plurality of points in time, an output of the eyelid occlusion sensor;
      determining, at a first point in time based on the detected output of the eyelid occlusion sensor, that a level of noise in the output of the eyelid occlusion sensor during a specified period of time prior to the first point in time is below a specified level;
      determining that a detected output of the eyelid occlusion sensor at the first point in time exceeds a first threshold; and
      responsive to determining (1) that the detected output of the eyelid occlusion sensor at the first point in time exceeds the first threshold, and (2) that the level of noise in the output of the eyelid occlusion sensor during the specified period of time prior to the first point in time is below the specified level, adjusting an optical power of the adjustable lens.

2. The ophthalmic device of claim 1, wherein adjusting the optical power of the adjustable lens comprises switching between a first optical power and a second optical power, wherein the first optical power is different than the second optical power.

3. The ophthalmic device of claim 1, wherein adjusting the optical power of the adjustable lens comprises setting the optical power of the adjustable lens to a first optical power, and wherein the operations further comprise:
   determining, at a second point in time based on the detected output of the eyelid occlusion sensor, that a level of noise in the output of the eyelid occlusion sensor during a specified period of time prior to the second point in time is below the specified level;
   determining that a detected output of the eyelid occlusion sensor at the second point in time exceeds the first threshold; and
   responsive to determining (1) that the detected output of the eyelid occlusion sensor at the second point in time exceeds the first threshold, and (2) that the level of noise in the output of the eyelid occlusion sensor during the specified period of time prior to the second point in time is below the specified level, setting the optical power of the adjustable lens to a second optical power, wherein the first optical power is different than the second optical power.

4. The ophthalmic device of claim 1, wherein adjusting the optical power of the adjustable lens comprises setting the optical power of the adjustable lens to a first optical power, and wherein the operations further comprise:
   determining, at a second point in time based on the detected output of the eyelid occlusion sensor, that a level of noise in the output of the eyelid occlusion sensor during a specified period of time prior to the second point in time is below the specified level;
   determining that a detected output of the eyelid occlusion sensor at the second point in time does not exceed a second threshold, wherein the first and second thresholds differ; and
   responsive to determining (1) that the detected output of the eyelid occlusion sensor at the second point in time does not exceed the second threshold, and (2) that the level of noise in the output of the eyelid occlusion sensor during the specified period of time prior to the second point in time is below the specified level, setting the optical power of the adjustable lens to a second optical power, wherein the first optical power is different than the second optical power.

5. The ophthalmic device of claim 1, wherein the controller comprises a noise detector, and wherein determining that the level of noise in the output of the eyelid occlusion sensor during the specified period of time prior to the first point in time is below the specified level comprises detecting an output of the noise detector.

6. The ophthalmic device of claim 1, wherein the controller comprises a comparator, and wherein determining that the detected output of the eyelid occlusion sensor at the first point in time exceeds the first threshold comprises detecting an output of the comparator.

7. The ophthalmic device of claim 1, wherein detecting an output of the eyelid occlusion sensor at a plurality of points in time comprises detecting the output of the occlusion sensor at a rate that is less than 40 Hertz.

8. A method comprising:
   detecting, at a plurality of points in time, an output of an eyelid occlusion sensor;
   determining, based on the detected output of the eyelid occlusion sensor, that a first gesture has occurred;
   responsive to determining that the first gesture has occurred, switching the optical power of an adjustable lens between a first optical power and a second optical power, wherein the first optical power is different than the second optical power;
   determining, based on the detected output of the eyelid occlusion sensor, that a second gesture has occurred; and
   responsive to determining that the second gesture has occurred, setting the optical power of the adjustable lens to the first optical power.

9. The method of claim 8, wherein the first gesture has a first duration, and wherein the second gesture has a second duration that is greater than the first duration.

10. The method of claim 9, wherein determining, based on the detected output of the eyelid occlusion sensor, that a first gesture has occurred comprises:
- determining, based on the detected output of the eyelid occlusion sensor, that a degree of occlusion of an eye increases during a first period of time; and
- determining that a detected output of the eyelid occlusion sensor at a first point in time differs from a detected output of the eyelid occlusion sensor at a second point in time by less than a specified amount, wherein the second point in time is after the first period of time.

11. The method of claim 9, wherein determining, based on the detected output of the eyelid occlusion sensor, that a first gesture has occurred comprises:
- determining, at a first point in time based on the detected output of the eyelid occlusion sensor, that a level of noise in the output of the eyelid occlusion sensor during a specified period of time prior to the first point in time is below a specified level; and
- determining that a detected output of the eyelid occlusion sensor at the first point in time exceeds a first threshold.

12. An ophthalmic device comprising:
- an eyelid occlusion sensor;
- an adjustable lens; and
- a controller, wherein the controller comprises electronics that perform operations comprising:
  - detecting, at a plurality of points in time, an output of the eyelid occlusion sensor;
  - determining, based on the detected output of the eyelid occlusion sensor, that a first gesture has occurred;
  - responsive to determining that the first gesture has occurred, switching the optical power of the adjustable lens between a first optical power and a second optical power, wherein the first optical power is different than the second optical power;
  - determining, based on the detected output of the eyelid occlusion sensor, that a second gesture has occurred; and
  - responsive to determining that the second gesture has occurred, setting the optical power of the adjustable lens to the first optical power.

13. The ophthalmic device of claim 12, wherein the first gesture has a first duration, and wherein the second gesture has a second duration that is greater than the first duration.

14. The ophthalmic device of claim 13, wherein determining, based on the detected output of the eyelid occlusion sensor, that a first gesture has occurred comprises:
- determining, based on the detected output of the eyelid occlusion sensor, that a degree of occlusion of an eye increases during a first period of time; and
- determining that a detected output of the eyelid occlusion sensor at a first point in time differs from a detected output of the eyelid occlusion sensor at a second point in time by less than a specified amount, wherein the second point in time is after the first period of time.

15. The ophthalmic device of claim 13, wherein determining, based on the detected output of the eyelid occlusion sensor, that a first gesture has occurred comprises:
- determining, at a first point in time based on the detected output of the eyelid occlusion sensor, that a level of noise in the output of the eyelid occlusion sensor during a specified period of time prior to the first point in time is below a specified level; and
- determining that a detected output of the eyelid occlusion sensor at the first point in time exceeds a first threshold.

* * * * *